US005469841A

United States Patent [19]
Kobayashi et al.

[11] Patent Number: 5,469,841
[45] Date of Patent: Nov. 28, 1995

[54] ENDOSCOPE APPARATUS PROVIDED WITH LIQUID REMOVING MECHANISM FOR THE ELECTRIC CONNECTOR

[75] Inventors: Kazunari Kobayashi; Kenji Omachi; Yutaka Tatsuno, all of Hachioji; Masahiro Hagihara, Shirakawa; Atsuki Kidawara, Tachikawa; Tadayoshi Hara; Nobuyoshi Yazawa, both of Hachioji, all of Japan

[73] Assignee: Olympus Optical Co., Ltd., Tokyo, Japan

[21] Appl. No.: 141,731

[22] Filed: Oct. 27, 1993

[30] Foreign Application Priority Data

| Oct. 29, 1992 | [JP] | Japan | 4-291745 |
| Feb. 24, 1993 | [JP] | Japan | 5-035807 |
| Feb. 24, 1993 | [JP] | Japan | 5-035808 |

[51] Int. Cl.$^6$ ................................................ A61B 1/06
[52] U.S. Cl. ........................................ 600/158; 600/182
[58] Field of Search ............................. 128/4–10; 606/15; 403/37; 385/117, 115; 439/190, 205, 196, 609, 907; 422/28

[56] References Cited

U.S. PATENT DOCUMENTS

| 3,906,953 | 9/1975 | Wallace et al. | 606/15 |
| 4,325,606 | 4/1982 | Ikuno et al. | |
| 4,611,872 | 9/1986 | Ito et al. | |
| 4,851,866 | 7/1989 | Ciarlei et al. | 128/4 X |
| 4,863,304 | 9/1989 | Bauer et al. | 128/4 X |
| 4,892,706 | 1/1990 | Kralovic et al. | 422/28 |
| 5,188,094 | 2/1993 | Adair | 128/6 |

FOREIGN PATENT DOCUMENTS

| 0207111 | 10/1985 | Japan | 128/6 |
| 60-184501 | 12/1985 | Japan. | |
| 0266314 | 10/1990 | Japan | 385/117 |

*Primary Examiner*—Richard J. Apley
*Assistant Examiner*—John P. Leubecker
*Attorney, Agent, or Firm*—Armstrong, Westerman, Hattori, McLeland & Naugthon

[57] ABSTRACT

An endoscope apparatus comprising an electrical connector which is electrically connected to an electrical device such as a CCD in an organism inserting device such as an endoscope which has an inserting section inserted into a organism. The electrical connector is connected to an electrical connector receptacle such as a control unit after the organism inserting device has been disinfected and sterilized by disinfection liquid. Processing is first performed in which the liquid remaining in the vicinity of an electrical contact of the electrical connector is removed by a liquid removing mechanism and, thereafter, electrical operation occurs. Thus, generation of a short-circuiting accident is prevented.

34 Claims, 21 Drawing Sheets

5,469,841

ENDOSCOPE APPARATUS PROVIDED WITH LIQUID REMOVING MECHANISM FOR THE ELECTRIC CONNECTOR

BACKGROUND OF THE INVENTION

1. Field of the Invention

The present invention relates to an endoscopic apparatus provided with a liquid removing mechanism for preventing electrical contacts from being short-circuited by liquid which is adhered to an electrical connector when components or instruments of the endoscope apparatus are connected to each other.

2. Description of the Related Art

In recent years, in the medical art field, an endoscope has been widely used in which an elongated inserting section is inserted into a body cavity to observe internal organs and the like within the body cavity. The endoscope is also used in industry to observe and inspect an object within a boiler, within tubes of a chemical plant, or within machines.

The endoscopic device includes an optical endoscope capable of performing observation using snake eyes from an ocular section, and an electronic endoscope in which a solid image pickup element such as a charge coupled device (CCD) or the like is arranged at an image pickup portion at a forward end of the inserting section. Normally, the endoscope is connected, through a connector, to a light-source unit for generating illuminating light to a subject, an image processing unit for processing an image pickup signal from the CCD of the electronic endoscope or a camera exterior-mounted on the ocular portion of an optical endoscope, an observation monitor for projecting an image signal processed by the image processing unit, or the like, and is formed as an endoscope apparatus and is used.

In particular, Japanese Utility Model Laid-Open No. SHO 60-184501 discloses and endoscopic device in which, in instruments dipped in liquid by cleaning, disinfection or the like such as the endoscope, the exterior-mounted camera and the like, the connector is also formed of a liquid-tight structure such that the liquid does not enter or invade the interior to cause a malfunction.

Specifically, as shown in FIG. 1 of the attached drawings, a prior art example has been disclosed in which a retractable electrode terminal pin 701 which is biased in a direction projecting from an outer peripheral surface is provided on an outer peripheral portion of a connector plug body 700 of an endoscope; a pair of sealing elements 702 and 703 are interposed in the rear of and in front of the electrode terminal pin 701; the sealing elements 702 and 703 are covered by a movable sleeve 704 which is biased axially, whereby the prior art example is arranged to be liquid-tight. In the connector of the prior art example, the arrangement is such that, when a plug of the endoscope is inserted into a socket of a control unit, the sleeve 704 is moved axially so that the electrode terminal pin 701 is released and is in contact with a mating electrode element whereby electric connection is made.

Further, Japanese Patent Laid-Open No. SHO 61-248017 discloses a connector for an endoscope, in which a waterproof chamber is provided on a rear side of an insulator which is provided with a pin contact such that a space is confronted against a proximal end of the pin contact, whereby, even if water enters the interior of the waterproof chamber through a gap between the pin contact and the insulator, the water remains within the waterproof chamber to prevent the water from further invading the interior thereof.

However, after the instrument has been dipped into the liquid such as water or the like by cleaning, disinfection or the like, the water or moisture is adhered to the connector of the instrument as a lump. Thus, wiping by a cloth or the like does not completely remove the moisture.

Accordingly, even in the instrument having the connector of the liquid-tight structure which is provided with the waterproof chamber at the proximal end of the pin contact or the connector in which the electric contact is covered with the sleeve, as in the aforesaid prior art example, when the instrument is wiped by the cloth or the like after the instrument has been dipped in the liquid such as water or the like by cleaning, disinfection or the like, and is immediately connected to the other instruments, a thin film of moisture still remains on the electrical contacts. Thus, there is a fear that the electrical contacts will conduct and be short-circuited.

SUMMARY OF THE INVENTION

It is an object of the invention to provide a unit for insertion into an organism of an endoscope apparatus or the like in which, even if moisture or liquid remains in a connector of an instrument dipped within liquid, electric contacts of connectors are not short-circuited when the unit is connected to other instruments.

It is another object of the invention to provide a unit for insertion into an organism, which is superior in operability and which is high in safety.

According to the present invention, there is provided a unit for insertion into an organism, such as an endoscope apparatus having an instrument in which an electrical connector is connected to an electrical connector receptacle to perform electrical connection therebetween, wherein liquid removing means is provided for removing liquid which is adhered to the vicinity of a plurality of electrical contacts on the side of the electrical connector by absorption drying or the like, and wherein electrical functioning is performed after the liquid has been removed by the liquid removing means, to prevent generation of an electrical failure from a short-circuit.

BRIEF DESCRIPTION OF THE DRAWINGS

FIGS. 2 to 5b relate to a first embodiment of the invention where:

FIG. 2 is an arrangement view of an endoscope apparatus according to the first embodiment of the invention;

FIG. 3 is an arrangement view showing a specific structure of FIG. 2;

FIGS. 5a and 5b show a CCU, FIG. 5a being an explanatory view showing a condition of dying processing in which electric connector is connected to an opening, and FIG. 5b being an explanatory view showing a condition in which, after drying processing, the electric connector is mounted on an electric connector receptacle;

FIG. 6 is an arrangement view showing an arrangement of an endoscope apparatus according to the second embodiment;

FIG. 7 is a schematic arrangement view of a CCU;

FIG. 9 is an entire arrangement view of an endoscope apparatus according to the third embodiment;

FIG. 10 is a block diagram showing an arrangement of a CCU;

FIG. 12 is an arrangement view of an endoscope apparatus according to the fourth embodiment;

FIG. 13 is a cross-sectional view showing a structure of an endoscope in which a TV camera is exterior-mounted;

FIG. 14 is a block diagram showing an arrangement of a CCU;

FIG. 15 is an arrangement view of an endoscope apparatus according to the modification;

FIG. 16 is a cross-sectional view showing a structure of an electronic endoscope;

FIGS. 17 to 19b relate to a fifth embodiment of the invention, where:

FIG. 17 is an entire arrangement view of an endoscope apparatus according to the fifth embodiment;

FIGS. 19a and 19b are cross-sectional views of an electrical connector receptacle in an unconnected condition and in a connected condition, respectively;

FIGS. 24 to 27b relate to a seventh embodiment of the invention, where:

FIG. 24 is an entire arrangement view of an endoscope apparatus according to the seventh embodiment;

FIG. 25 is a cross-sectional view showing a structure of an electrical connector;

FIG. 26 is a cross-sectional view showing a condition under which the electrical connector is mounted on an electrical connector receptacle;

FIGS. 27a and 27b are cross-sectional views showing an unconnected, gas-feeding connector and a connected gas-feeding connector, respectively;

FIG. 28 is a cross-sectional view showing a structure of an electrical connector and an electrical receptacle in the eighth embodiment;

FIG. 29 is a cross-sectional view showing the electrical connector being connected to the electrical connector receptacle;

DETAILED DESCRIPTION OF THE PREFERRED EMBODIMENTS

Various embodiments of the invention will hereinafter be described with reference to the accompanying drawings.

Figure 1:
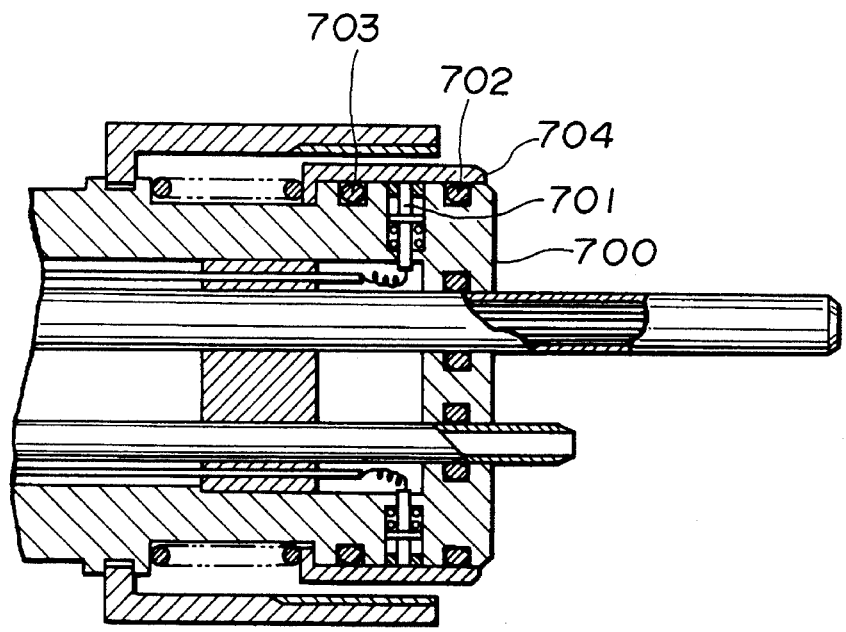
FIG. 1 is a cross-sectional view of an electrical plug in a prior art example.
Figure 2:
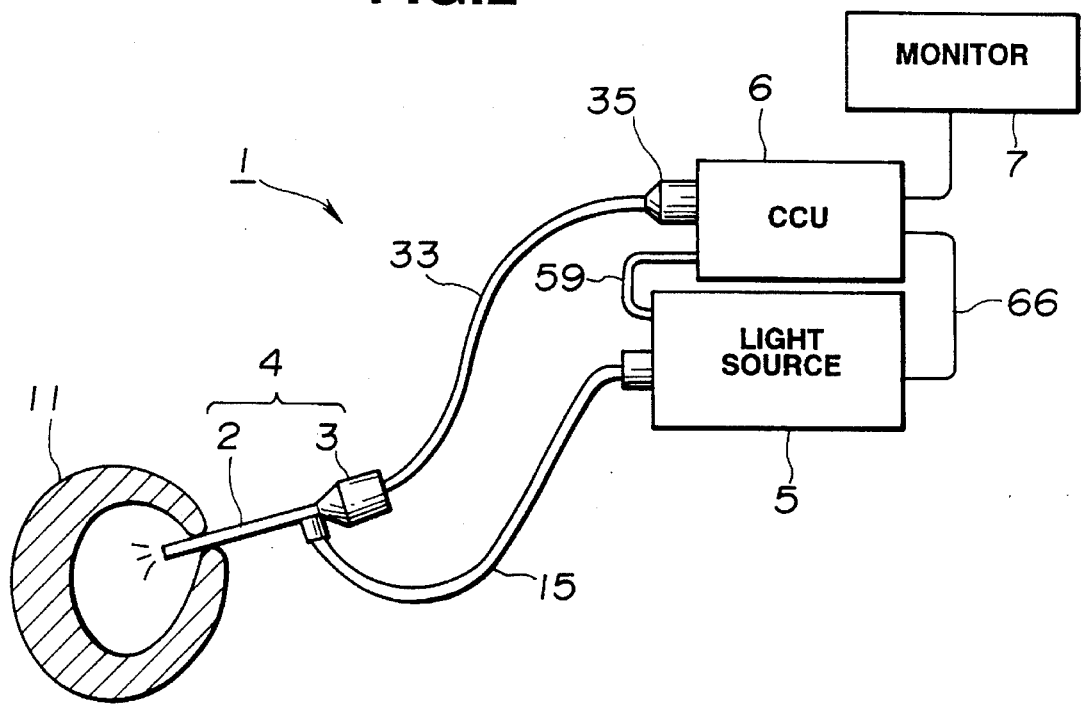

Referring to FIG. 2, and endoscope apparatus 1 according to a first embodiment of the present invention comprises an endoscope 4 of a system in which a TV camera is exterior-mounted (serving as an organism insertion device inserted into an organism) including a rigid endoscope 2 having an elongated rigid inserting section 8 and a TV camera 3 which is mounted on an ocular portion 10 of the rigid endoscope 2, a light-source unit 5 for supplying illuminating light to the rigid endoscope 2, a camera control unit (hereinafter briefly referred to as "CCU") 6 for performing a signal processing with respect to the TV camera 3, and a color monitor 7 for displaying an image signal which is outputted from the CCU 6.

Figure 3:
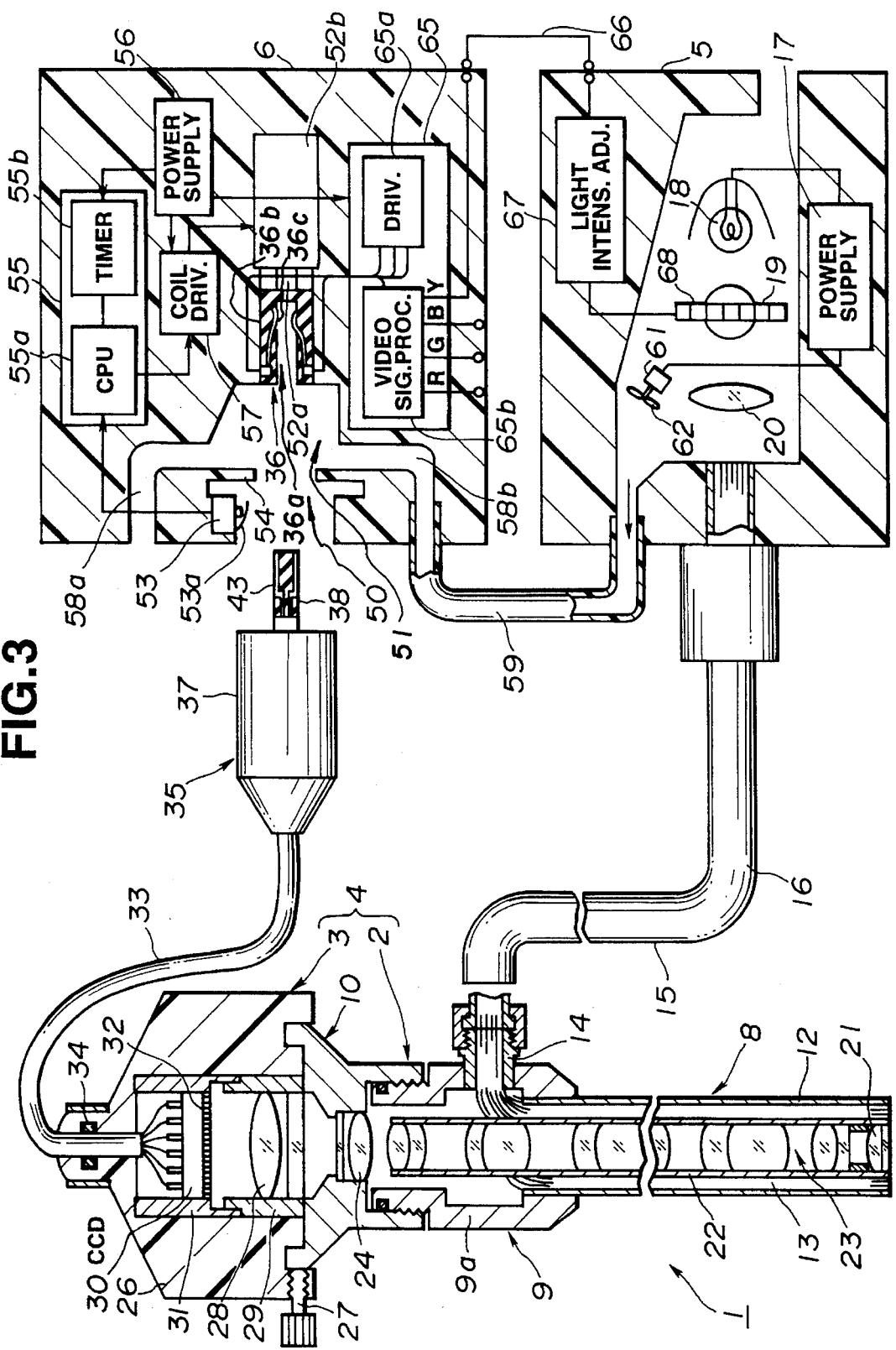

As shown in FIG. 3, the rigid endoscope 2 comprises the elongated rigid inserting section 8 formed by a metallic cylindrical pipe 12, a gripping portion 9 increasing in diameter arranged at a proximal end of the inserting section 8, and the conical ocular portion 10 arranged at a rear end of the gripping portion 9. The inserting section 8 is inserted into the interior of a subject 11 through a small piercing bore or the like formed in the abdomen or the like of the subject 11 serving as an organism.

A light guide 13 formed by a fiber bundle for transmitting illuminating light is inserted into the cylindrical overcoat pipe 12 which forms the inserting section 8. The light guide 13 has a rearward end thereof which reaches a light guide base 14 which is bent at the gripping portion 9.

The base 14 is forcedly fitted into an opening which is provided in a side surface of a frame 9a of the gripping portion 9. The base 14 is fixedly mounted on the frame 9a by soldering. The base 14 consists of a liquid-tight and moisture-proof structure in which liquid and moisture cannot invade the interior of the opening.

A light guide cable 15 having resiliency or elasticity has one end thereof which is connected to the light guide base 14. A light guide connector 16 provided on the other end of the cable 15 can be detachably mounted on the light source unit 5. A lamp 18 emitting light by electric power supplied from a power supply 17 is accommodated or received within the light source unit 5. Illuminating light from the lamp 18 is irradiated upon an end surface of the light guide connector 16 through an iris or stop 19 and a condenser lens 20.

The illuminating light irradiated upon the end surface is transmitted by a light guide within the light guide cable 15, and is supplied to the light guide 13 within the rigid endoscope 2 from the light guide base 14. The illuminating light transmitted by the light guide 13 projected forwardly from a forward end surface of the inserting section 8 which is fixedly mounted on an illuminating window at a forward end of the inserting section 8 to illuminate an affected or diseased part within the subject 11.

The illuminated part, such as the affected part or the like, forms an optical image on a focal plane of an objective lens 21 mounted on an observation window, which is provided at the forward end of the inserting section 8, by the objective lens 21. The objective lens 21 is mounted in the vicinity of a forward end of a lens receiving tube 22 which is arranged concentrically within the overcoat pipe 12. A cover glass material is mounted in front of the objective lens 21 so that the observation window is brought to a liquid-tight and gas-tight structure. Moreover, an illuminating window is also mounted on the water-proof and gas-tight structure by an adhesive or the like, on which the light guide 13 is mounted.

An optical image due to the objective lens 21 is transmitted rearwardly by an image guide formed by a relay optical system 23 which is received within the lens receiving tube 22 and which is arranged on an optical axis of the objective lens 21. The relay optical system 23 is arranged within the inserting section 8 and the gripper portion 9. An ocular lens 24 is arranged within the ocular portion 10 in opposed relation to a rearward end of the relay optical system 23. The ocular portion 10 is connected to the frame 9a of the gripper portion 9 by a threadedly engaging mechanism.

A sealing O-ring is interposed at the connecting portion to form a water-proof structure in which liquid does not enter the interior of the connecting portion therefrom and a moisture-proof structure in which steam does not enter the interior thereof. Furthermore, the ocular portion 10 has an ocular window which is closed by a cover glass material, and forms a liquid-tight structure in which liquid does not enter the interior thereof and a moisture-proof structure in which steam does not enter the interior thereof.

The optical image transmitted by the relay optical system 23 can be observed in enlargement from the ocular window through the ocular lens 24.

As described above, the rigid endoscope 2 is brought to the liquid-tight and moisture-proof structure so that the rigid endoscope 2 can be dipped within chemicals so as to be disinfected or sterilized, or can be dipped within the cleaning liquid, and the like, so as also to be cleaned.

The TV camera 3 has a head frame 26 which is detachably mounted on the ocular portion 10 by a fixing screw 27. An imaging lens 28 is fixedly mounted on an opening opposed against the ocular window in the head frame 26, through a lens frame 29. The opening is closed by the cover glass material 29 so as to be brought to a liquid-tight structure in which liquid does not enter the interior thereof and to a moisture-proof structure in which steam does not enter the interior thereof.

A CCD frame 31 on which a charge coupled device (hereinafter referred to as "CCD") 30 serving as an electric device is mounted is connected to a rearward end of the lens frame 29, and is fixed by screws (not shown). The optical image transmitted by the relay optical system 23 is imaged onto an image pickup surface (photoelectrically conversation surface) of the CCD 30 through the ocular lens 24 and the imaging lens 28. A color separation filter 32 is mounted on the image pickup surface of the CCD 30. The optical image which is color-separated into R, G and B for every pixel, for example, is imaged onto the image pickup surface of the CCD 30.

A signal transmitting cable 33 has a plurality of signal lines which are connected respectively to a plurality of leads, by soldering, which project onto a rear surface of the CCD 30. The signal transmitting cable 33 passes through a bore in the head frame 26 and extends to the outside. A sealing O-ring 34 is interposed on the way of the bore, and a ring is mounted on a projecting portion of the rear end of the head frame 26 by caulking such that a biasing force crushing the O-ring 34 acts on or is applied to, so that a liquid-tight structure is formed in which liquid does not enter the interior of the bore and a moisture-proof structure is formed in which steam does not enter the interior of the bore.

Figure 4A:
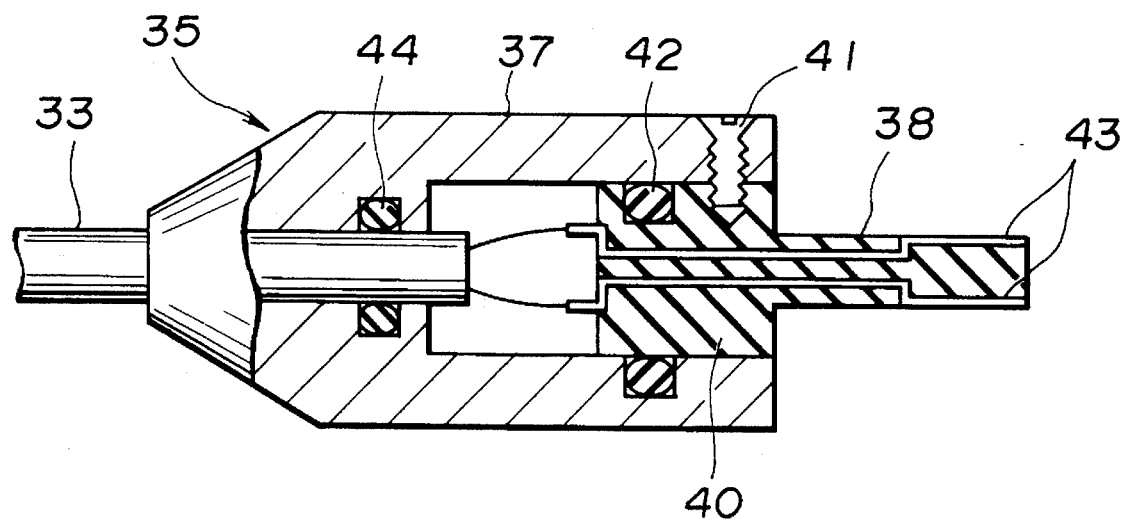
FIGS. 4a and 4b are a side-surface cross-sectional view and a top plan view of an electric connector, respectively.
Figure 4B:
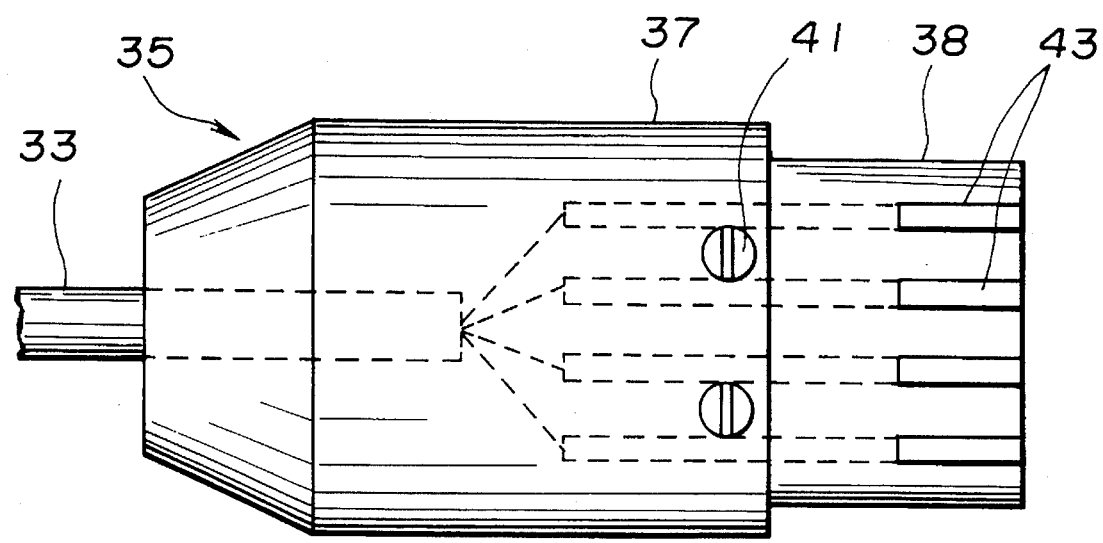

The signal transmitting cable 33 which extends to the outside has a distal end on which an electric connector 35 is mounted. The electric connector 35 can be detachably mounted on an electric connector receptacle 36 of the CCU 6. The electrical connector 35 is a connector of a card edge type, as shown in FIGS. 4a and 4b, in which a connector portion 38 in the form of a card (thin sheet) projects from a forward end of a connector body 37. The connector portion 38 has a thickened proximal end 40 which is fitted into a recess in the metallic connector body 37, and which is fixedly mounted by a fixing screw 41. A sealing O-ring 42 is interposed at a portion which is fitted into the connector body 37 so as to be brought to a liquid-tight and moisture-proof structure.

A plurality of electrical contacts 43 are embedded within the connector portion 38 which is formed by an insulator. The electrical contacts 43 have respective forward ends thereof which are exposed flush to both surfaces (upper and lower both surfaces in FIG. 4a) of a card of the connector portion 38. The electrical contacts 43 have respective rearward ends thereof which are exposed rearwardly of the proximal end 40. The rearward ends pass through the bore in the connector body 37, and signal lines drawn out of the distal end of the signal cable 33 received within the recess are connected respectively to the rearward ends by soldering.

A sealing O-ring 44 is also interposed on the way of the bore in the connector body 37 so as to be brought to a liquid-tight and moisture-proof structure.

As described above, the TV camera 3 which is mounted on the ocular portion 10 of the rigid endoscope 2 is also brought to a water-proof and moisture-proof structure, so that the TV camera 3 can be dipped within chemicals so as to be sterilized and can be dipped within cleaning liquid, and the like, so as to be cleaned.

A structure of the CCU 6 on which the electrical connector 35 at the distal end of the signal transmitting cable 33 of the TV camera 3 is detachably mounted will next be described.

A drying and removing mechanism 51 for drying and removing moisture adhered to the electric connector 35 is arranged within an opening 50 which is provided in the front surface of the CCU 6. The electrical connector receptacle 36 is arranged on the interior of the opening 50 under such a condition that the electrical connector receptacle 36 is mounted on a plunger 52a. The electrical connector 35 is first dried and removed by the drying and removing mechanism 51 and, thereafter, is connected to the electrical connector receptacle 36 which is moved forwardly by movement of the plunger 52.

Figure 5A:
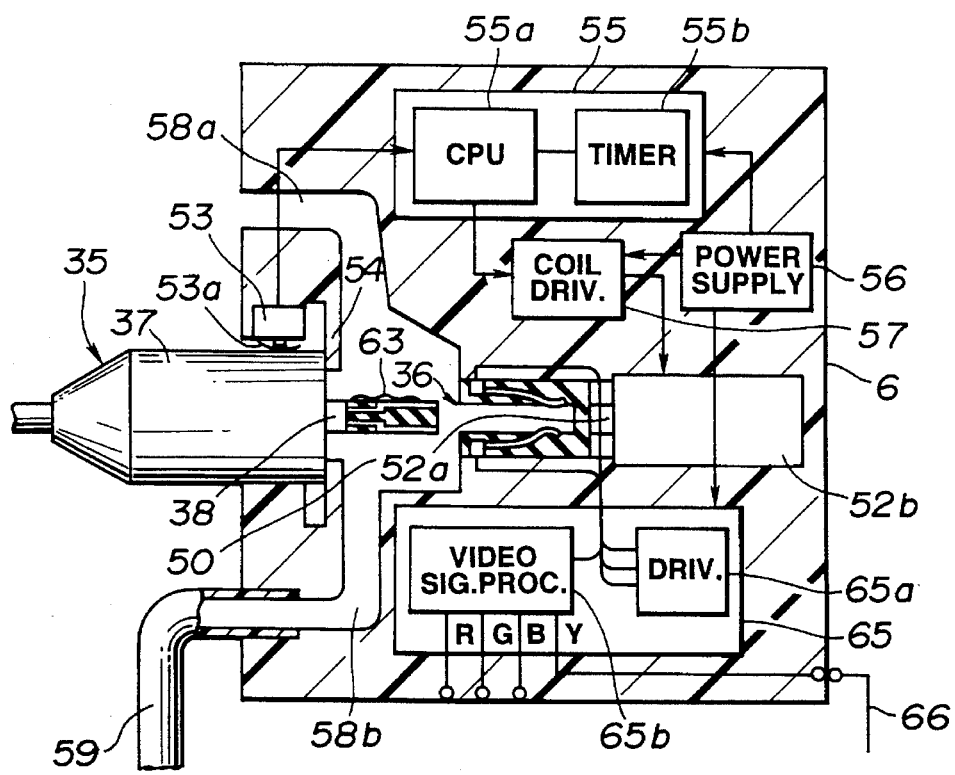
Figure 5B:
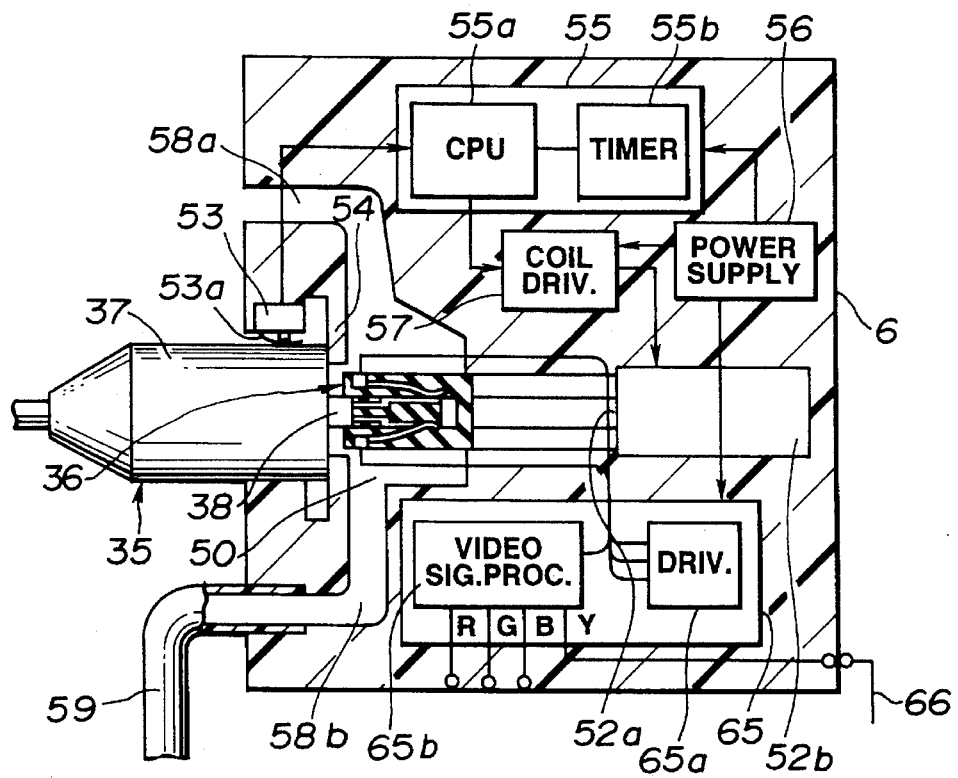

The electrical connector receptacle 36 has a plurality of contacts 36c embedded in an insulator 36b provided with an opening 36a which is fitted into the connector portion 38, such that the plurality of electrical contacts 36c are exposed toward the opening 36a. The electrical contacts 43 of the connector portion 38 are conducted respectively to the electrical contacts 36c of the electrical connector receptacle 36 under a condition that, as shown in FIG. 5b, the connector portion 38 is received into the opening 36a.

A portion in the vicinity of an entrance of the opening 50 is brought to a configuration into which the electrical connector 35 is capable of being inserted. A switch lever 53a of a micro switch 53, for example, is provided on an inner wall surface in the vicinity of the entrance of the opening 50 so as to project inwardly of the opening 50. As shown in FIG. 5a, a setting is made such that, when the electrical connector 35 is inserted, the switch lever 53a is pressed or urged by an outer surface of the connector body 37 of the electrical connector 35 so that the micro switch 53 is turned ON.

A projection 54 is provided at a position adjacent to the micro switch 53 within the opening 50 and on a side opposed against the position. The inserted electrical connector 35 is regulated in position such that the front surface of the connector body 36 is abutted against projections 54.

The micro switch 53 is connected to a CPU 55a which forms a control circuit 55. The CPU 55a performs control such that, when the micro switch 53 is turned ON, current is supplied to an electromagnetic coil 52b from an electrical power supply 56 through a coil driver 57 after a setting time set by a timer 55b. The electromagnetic coil 52b projects the plunger 52a (against a spring (not shown)) to move the electrical connector receptacle 36 forwardly so that the electromagnetic coil 52b is mounted on the electrical connector 35 (refer to FIG. 5b).

An exhaust passage 58a and a gas-feeding passage 58b are provided respectively in upper and lower wall surfaces, for example, within the opening 50. The gas-feeding passage 58b is connected to the light source unit 25 through a gas-feeding tube 59. A fan 62 rotatively driven by a motor 61 is arranged within the light source unit 25 at position above, for example, the lens 20. Heat generated by the lamp 18 or the like is emitted or exhausted from the opening through the tube 59. Air including the heat exhausted (hereinafter referred to as "heated air") is fed into the CCU 6 and is utilized for liquid removal of the electrical connector 35.

As shown in FIG. 5a, heated air is blown against the connector portion 38 from an underneath which is opposed against the connector portion 38. A surface of the connector portion 38, for example, is vaporized or evaporated by the heated air even if moisture 63 of the cleaning liquid remains, and the moisture 63 is emitted or released to the outside through the exhaust passage 58a. Accordingly, the moisture 63 is removed after a while form the fact that the electrical connector 35 is mounted in the opening 50, so that the connector portion 38 is fully dried.

Timer 55b allows sufficient drying time to elapse. The elapsed time is transmitted to the CPU 55a. The CPU 55a causes current to flow to the electromagnetic coil 52b through the coil driver 57. Then, the plunger 52a formed by a magnet is moved forwardly together with the electrical connector receptacle 36 mounted on the forward end, by a magnetic repulsion force or the like.

As illustrated in FIG. 5b, the electrical connector receptacle 36 is connected to the electrical connector 35. The electrical contacts 43 of the electrical connector 35 are in contact with the electrical contacts 36c of the electrical connector receptacle 36, respectively, and are brought to a condition electrically conducted thereto.

In FIG. 3, the electrical contacts of the electrical connector receptacle 36 are connected to the CCD drive circuit 65a and the video-signal processing circuit 65b which cooperate with each other to form the signal processing circuit 65. In a case where the electrical connector 35 is connected to the electrical connector receptacle 36, the drive signal is applied to the CCD 30 from the CCD drive circuit 65a, and the CCD output signal photoelectrically converted by the CCD 30 is inputted to the video-signal processing circuit 65b. Signal processing with respect to the CCD output signal is performed by the video-signal processing circuit 65b. A three-primary-color signal, including R, G and B colors, is generated as a standard image signal which is outputted to the color monitor 7.

The video-signal processing circuit 65B generates also the intensity signal Y. The intensity signal Y is inputted to the light-quantity adjusting or regulating circuit 67 of the light-source unit 5 through the cable 66.

The light-intensity adjusting circuit 67 integrates the intensity signal Y for a single frame duration, for example, to generate an integrating signal. The light-intensity adjusting circuit 67 compares the integrating signal with a reference voltage corresponding to a reference brightness to generate an error signal from the reference voltage. The error signal is applied to the motor 68 through the drive circuit. The light-intensity adjusting circuit 67 control the rotational angle of the stop 19 to control the passage amount of the illuminating light quantity, to thereby perform light-intensity control such that the illuminating light intensity is brought to an adequate light intensity.

For example, if the level of the intensity signal Y is excessively large, the motor 68 is rotated by the error signal in such a direction that the passage light quantity of the stop 19 decreases. Thus, the motor 68 is set to an adequate illuminating light intensity. Conversely, if the level of the intensity signal Y is excessively small, the motor 68 is rotated by the error signal in such a direction that the passage light intensity of the stop 19 increases. Thus, the motor 68 is set to an adequate illuminating light intensity. In FIG. 3, the stop 19 is formed in such a manner that small hexagonal rings are stacked upon each other. FIG. 3 shows an open condition under which the illuminating light passes without being substantially shielded. When the stop 19 is rotated from this condition and is inclined, the light is shielded by wall surfaces of the hexagonal rings so that the passage light intensity decreases.

In the present embodiment, the electrical connector 35 is connected to the electrical connector receptacle 36 after the connector portion 38 thereof has been dried for a predetermined period of time. Accordingly, even if the surface of the connector portion 38 is connected to the opening 50 under a condition humidified by the moisture 63 (refer to FIG. 5a), the connector portion 38 is connected to the opening 36a in the electrical connector receptacle 36 after the moisture 63 has been removed. Accordingly, even when the current is supplied toward the electrical connector receptacle 36, a failure produced by excessive current or the like flowing through the electrical contacts 43 causing a short-circuit because the moisture 63 has been removed.

Figure 6:
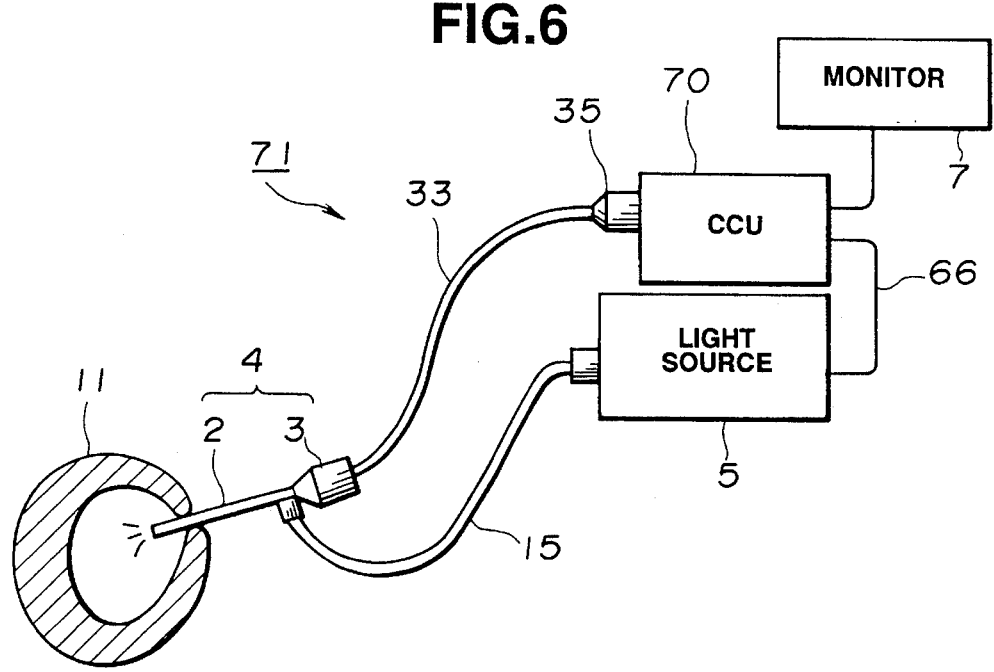
FIGS. 6 and 7 relate to a second embodiment of the invention, where.

In the first embodiment, the heat produced by the heat radiating mechanism which emits or releases the heat generated by the light source unit 5 is utilized to form the liquid removing mechanism for performing removal of the moisture. In a second embodiment illustrated in FIG. 6, heat generated within a CCU 70, for example, is utilized to form a liquid removal mechanism. An endoscope apparatus 71 illustrated in FIG. 6 has a structure lacking any tube connecting the CCU 6 and the light source unit 5 in FIG. 2 to each other. An arrangement of the CCU 70 in the present embodiment is shown in FIG. 7.

Figure 7:
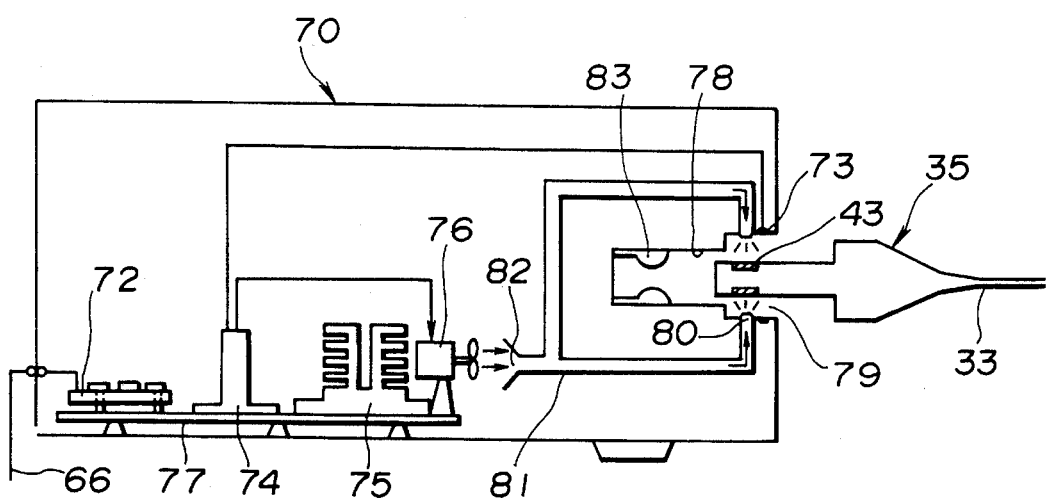

The arrangement of an electrical connector 35 which is used in FIG. 7 is substantially the same as that illustrated in FIG. 4. Within the CCU 70, a circuit board or substrate 72 forming a signal processing circuit 65, a fan drive unit 74 electrically connected to a sensor 73, a heat sink 75, and a fan 76 provided in the vicinity of the heat sink 75 are fixedly mounted on an identical table 77 made of a heat transmitting element, by screws or the like (not shown). The other end of a pipe 81 having an opening 80 at a location inside the sensor 73 which is provided at an entrance 79 of an electrical connector receptacle 78 is formed into an introduction bore 82 which is opposed against the fan 76. Further, the fan 76 is electrically connected to the fan drive unit 74. An electrical contact 83 arranged to be in contact with an electrical contact 43 is received at a deep portion of the electrical connector receptacle 78, and is connected to the circuit substrate 72 by a signal line (not shown).

With the arrangement described above, when the electrical connector 35 to which a small quantity liquid is adhered is inserted into the electrical connector receptacle 78, the sensor 73 detects approaching of the electrical connector 35 to transmit a detecting signal thereof to the fan drive unit 74 so that the fan drive unit 74 activates the fan 76.

In this case, since heat generated by the circuit substrate 72 is transmitted through a table 77 and is radiated from the heat sink 75, the fan 76 provided in the vicinity of the heat sink 75 can send a hot wind to the introduction bore 82 in the pipe 81. The hot wind sent into the pipe 81 is jetted in the form of an air shower from the opening 80 which is provided in the vicinity of the inlet 79 of the electrical connector receptacle 78. The remaining liquid adhering to the surface of the electrical connector 35 including the electrical contact 43 is dried and removed. In this manner, since the present arrangement utilizes the heat generated within the CCU 70 to dry the electrical contact 43, the present arrangement can efficiently remove the remaining drops on the electrical contact 43 to prevent electrical short-circuiting from occurring.

Figure 8:
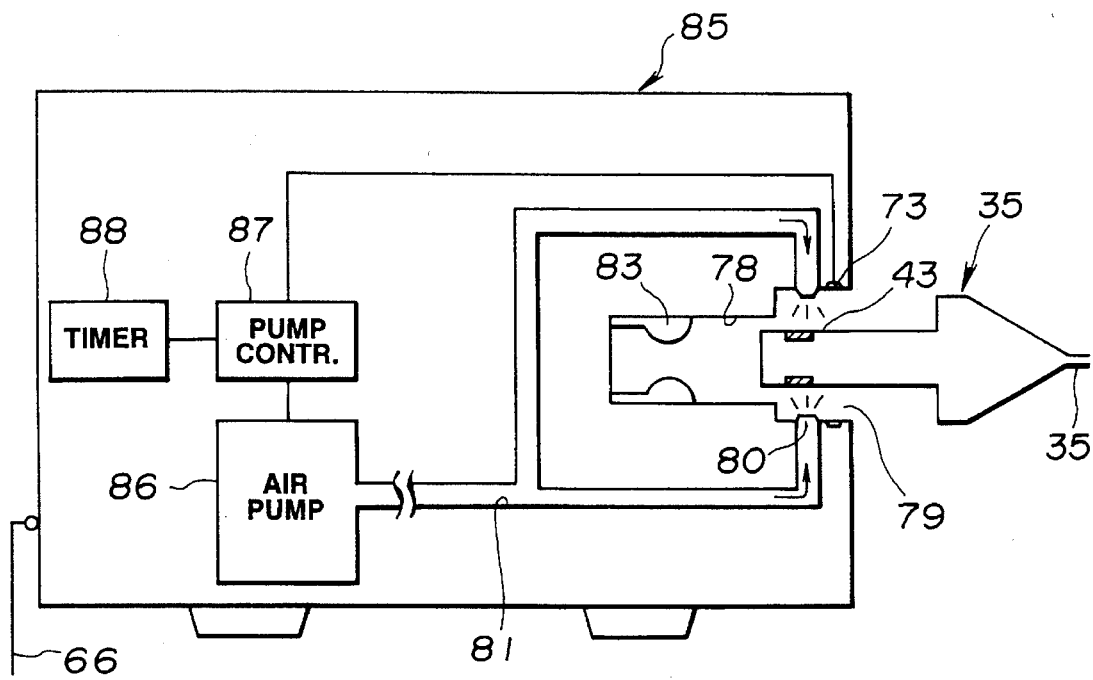
FIG. 8 is a cross-sectional view showing an arrangement of a CCU in a modification of the second embodiment.

FIG. 8 shows an arrangement of a CCU 85 in a modification of the second embodiment. In the second embodiment, heat generated from a circuit substrate 72 is utilized. However, in the modification, an air pump 86 is received within the CCU 85. Air within the air pump 86 is jetted into an inlet portion 79 from one opening 80 through a pipe 81 in which the other opening is connected to a discharge bore of the air pump 86, so that an electrical connector 35 is dried.

A sensor 73 is provided at the inlet portion 79 similarly to the second embodiment. When the sensor 73 detects insertion of the electric connector 35 into the inlet portion 79, the sensor 73 outputs a detecting signal to an air pump control 87.

The air pump controller 87 is electrically connected to the air pump 86, and activates the air pump 86 by the detecting signal. A driving time of the air pump 86, that is, a blowing time of the air, is set by a timer 88.

In connection with the above, the opening 80 of the pipe 81 which opens in the vicinity of the inlet portion 79 of an electrical connector receptacle 78 similarly to the second embodiment is positioned inside the sensor 73.

With the arrangement described above, when the electrical connector 35 to which the liquid is adhered, although a small quantity, is inserted into the electrical connector receptacle 78, the sensor 73 detects approaching of the electrical connector 35, to transmit a detecting signal thereof to the air pump controller 87. Thus, the air pump controller 87 activates the air pump 86 so that the air is sent out into the pipe 81 from the discharge bore in the air pump 86.

The air sent out into the pipe 81 is jetted in the form of an air shower from the opening 80 which is provided in the vicinity of the inlet portion 79 of the electrical connector receptacle 78, to remove the remaining liquid which is adhered to the surface of the electrical connector 35 including electrical contact 43.

In this manner, the present arrangement is low in cost because it utilizes parts having a wide use, and the remaining amount of liquid is completely removed so that it is possible to prevent an electrical short-circuit.

Figure 9:
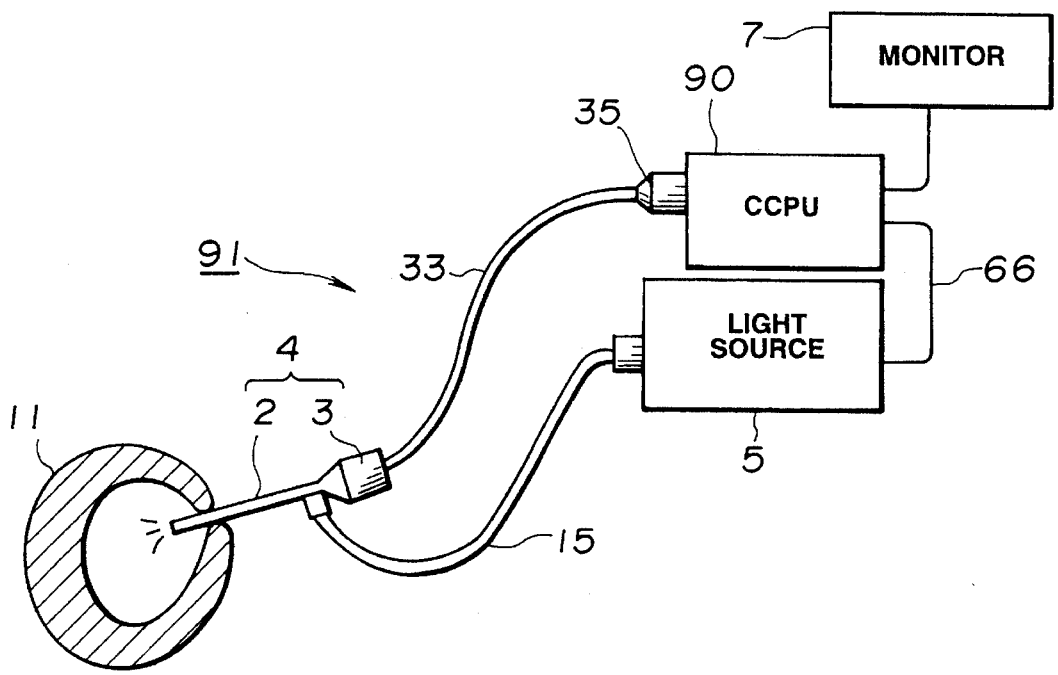
FIGS. 9 and 10 relate to a third embodiment of the invention, where.

FIG. 9 shows an endoscope apparatus 91 according to a third embodiment of the invention. In the second embodiment, before the electrical contact 43 of the electrical connector 35 is connected to the electrical contact 83 of the electrical connector receptacle 78, the electrical connector 35 is dried by the hot wind. However, in the present embodiment, drying processing is performed even when an electrical contact 43 of an electrical connector 35 is connected to an electrical contacted 83 of an electrical connector receptacle 78. The arrangement is such that, after the drying processing, the electrical contact 83 of the electrical connector receptacle 78 is electrically connected to a signal processing circuit 65. For this reason, the third embodiment has a CCU 90 different in arrangement from that of the second embodiment.

Figure 10A:
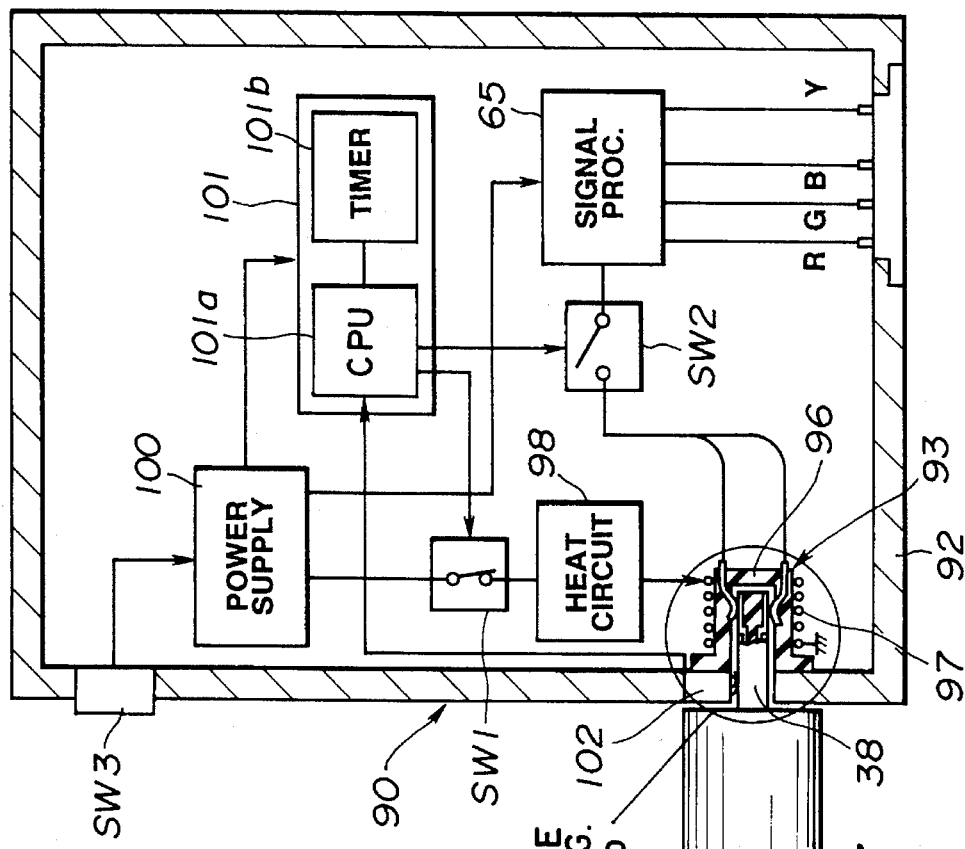
Figure 10B:
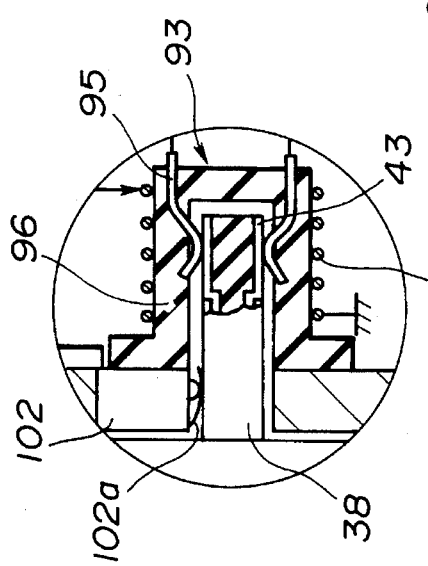

FIG. 10 shows an arrangement of the CCU 90 in the present embodiment.

An electrical connector receptacle 93 provided with a recess which is capable of receiving a connector portion 38 of an electrical connector 35 is mounted on a front surface of a housing 92 of the CCU 90. An electrical contact receptacle 95 which is in contact with the electrical contact 43 on the side of the electrical connector 35 so as to be conducted thereto is embedded within an insulator 96 on the side of the electrical connector receptacle 93, and a part of the electrical contact receptacle 95 is exposed within the recess.

A heating wire 97, for example, is wound around the periphery of the insulator 96, and heating current is supplied thereto from a heating circuit 98. The heating circuit 98 is connected to a power supply circuit 100 through a switch SW1. When the switch SW1 which is controlled in ON/OFF by a switching control circuit 101 is turned ON, the heating current is supplied to a heating wire 97.

Further, the electrical contact 95 on the side of the electrical connector receptacle 93 is connected to a signal processing circuit 65 through a switch SW2. When the switch SW2 which is controlled in ON/OFF by the switching control circuit 101 is turned ON, the signal processing circuit 65 is electrically connected to the CCD 30 (refer to FIG. 3) within the TV camera 3, to perform image signal processing to output a standard image signal to the color monitor 7 which is connected to an output end thereof.

A micro switch 102 is arranged adjacent to an electrical connector receptacle 93, for example, such that a lever 102a projects into the recess in which the connector portion 38 of the electrical connector 35 is received. When the connector portion 38 is received, the lever 102a is depressed so that the switch is turned ON. The micro switch 102 is connected to a CPU 101a which forms the switching control circuit 101. When the CPU 101a detects turning-ON, the CPU 101a judges that the electrical connector 35 is connected to the electrical connector receptacle 93, to turn ON the switch SW1 through a time set by a timer 101b, to thereby heat the heating wire 97 to cause the connector portion 38 to perform operation of liquid removal or moisture removal.

After a time which is set to provide a time period sufficient for operation of the liquid removal or moisture removal, the CPU 101a turns OFF the switch SW1 by the timer output, and turns ON the switch SW2 so that the CCD 30 is conducted to the signal processing circuit 65.

The power supply circuit 100 is turned ON by operation of a power source SW3, to supply electrical power having a predetermined voltage activating the switching control circuit 101 and the signal processing circuit 65.

In the first embodiment, the electrical connector 35 is restricted in position to a position short of the fact that the electrical connector 35 is connected to the electrical connector receptacle 36, to perform processing of liquid removal, and is capable of being connected to the electrical connector receptacle 36 after the processing, whereas, in the present embodiment, processing of moisture removal is also performed when the electrical connector 35 is mechanically connected to the electrical connector receptacle 36.

Moreover, in the present embodiment, the time period through which processing of liquid removal is performed is that in which the switch SW2 is turned OFF so that a drive signal is not applied to an electrical contact 43 connected to the CCD 30, and a drive-signal output end (and an input end for the CCD output signal) of the signal processing circuit 65 is brought to a release condition. Accordingly, even if there is a short-circuited condition between the two (2) electrical contacts 43 and 43 caused by moisture in a time period through which processing of the moisture removal is performed, current is not supplied to the CCD 30. Accordingly, actual damage caused by an electrical short-circuit is not generated. Furthermore, since a signal terminal of the signal processing circuit 65 is under a release condition, destruction due to short-circuiting is not generated.

In connection with the above, the switch SW1 may be provided on the side of an output of the heating circuit 98, and the switch SW2 may be provided between the power source circuit 100 and the signal processing circuit 65.

In a case where an operation in which the power source switch SW3 is turned ON is performed after the electrical connector 35 has been connected to the electrical connector receptacle 93, the micro switch 102 is not necessarily required.

Figure 11A:
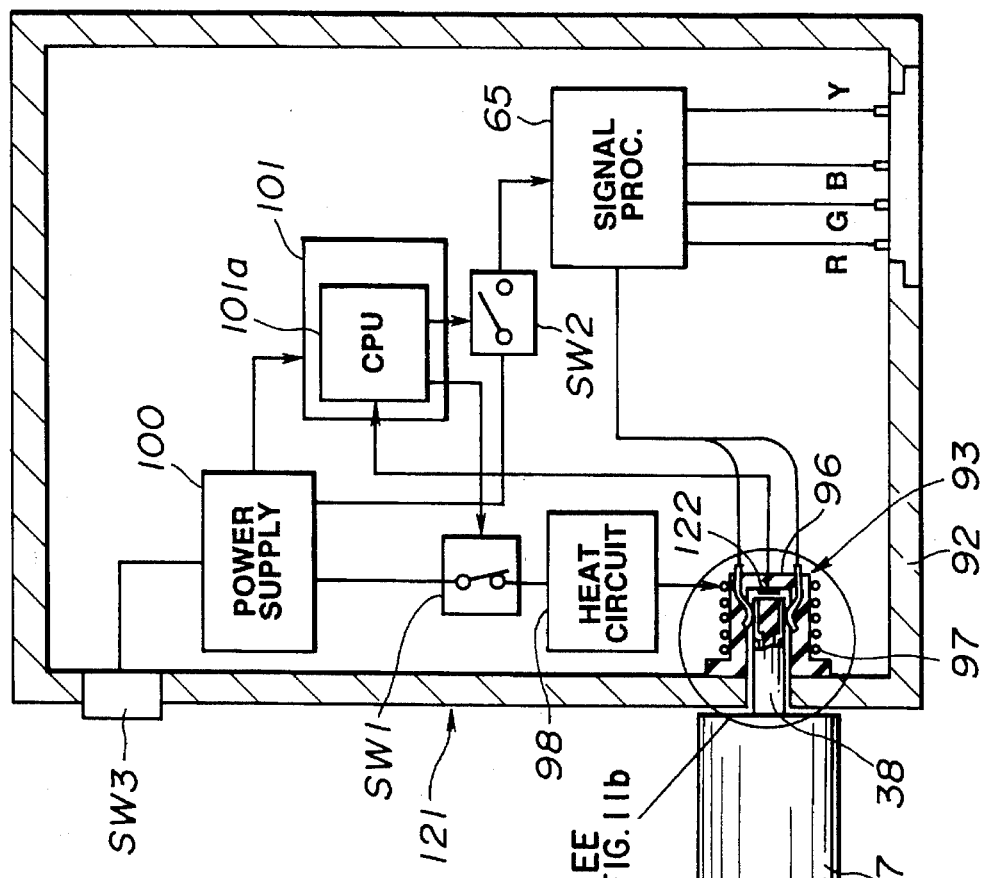
FIG. 11 is a block diagram showing an arrangement of a CCU in a modification of the third embodiment.
Figure 11B:
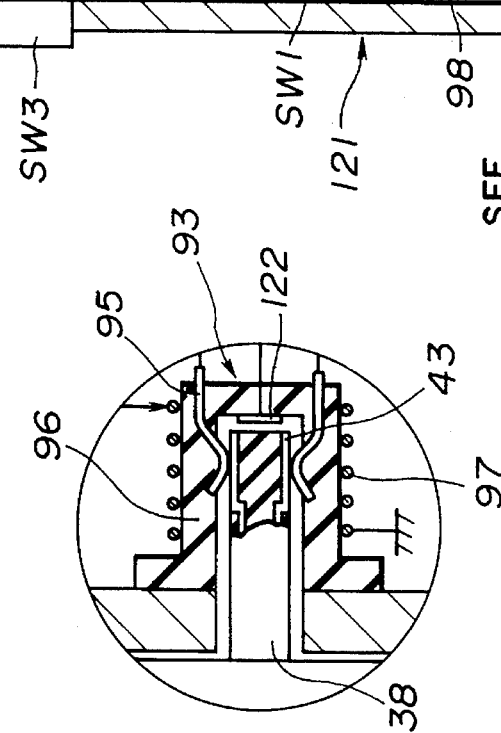

FIG. 11 shows a CCU 121 in a modification of the third embodiment. The modification is arranged such that the micro switch 102 in FIG. 10 is not provided, and a liquid detecting sensor 122 is provided within a recess in the electrical connector receptacle 93, for example, so that moisture within the recess in the electrical connector receptacle 93 is detected. An output from the sensor 122 is inputted to the CPU 101a which forms the switching control circuit 101.

The CPU 101a turns ON the switch SW1 and turns OFF the switch SW2 in a case where the sensor 122 detects moisture. Further, in a case where moisture is not detected, the switch SW1 is turned OFF, and the switch SW 2 is turned ON.

Moreover, in the modification, switch SW2 is provided between the power supply circuit 100 and the signal processing circuit 65. When the switch SW2 is turned OFF, current is not supplied to the signal processing circuit 65. Current is also not supplied to the side of the electrical connector 35 and the electrical connector receptacle 93 which are connected to the signal processing circuit 65. The other arrangements are the same as that shown in FIG. 10.

In the arrangement, when the power source switch SW3 is turned on, the order of the moisture within the recess in the electrical connector receptacle 93 is first detected by the sensor 122. By information thereof, the liquid removal mechanism is activated if the CPU 101a judges that there is the possibility that short circuiting has occurred. Meanwhile, if the order of the moisture is sufficiently low so that it is judged that short circuiting has not occurred, the switch SW2 is turned ON so that the signal processing circuit 65 is activated.

Accordingly, even if the pair of electrical contacts 43 and 43 is short-circuited by the moisture in a time the processing of the liquid removal is performed, the current is not supplied to the signal processing circuit 65 and the CCD 30. Thus, damage from short-circuiting is not generated.

The modification removes the liquid until no moisture is detected. If the moisture is not detected when the electrical connector 35 is mechanically connected to the electrical connector receptacle 93, removal of the liquid is not performed, but the CCD 30 is immediately connected electrically to the signal processing circuit 65. Signal processing with respect to the detected image is performed. The detected image is displayed on a display unit. The modification performs adequate removal of the liquid in accordance with the order of the moisture which is detected by the sensor 122.

Figure 12:
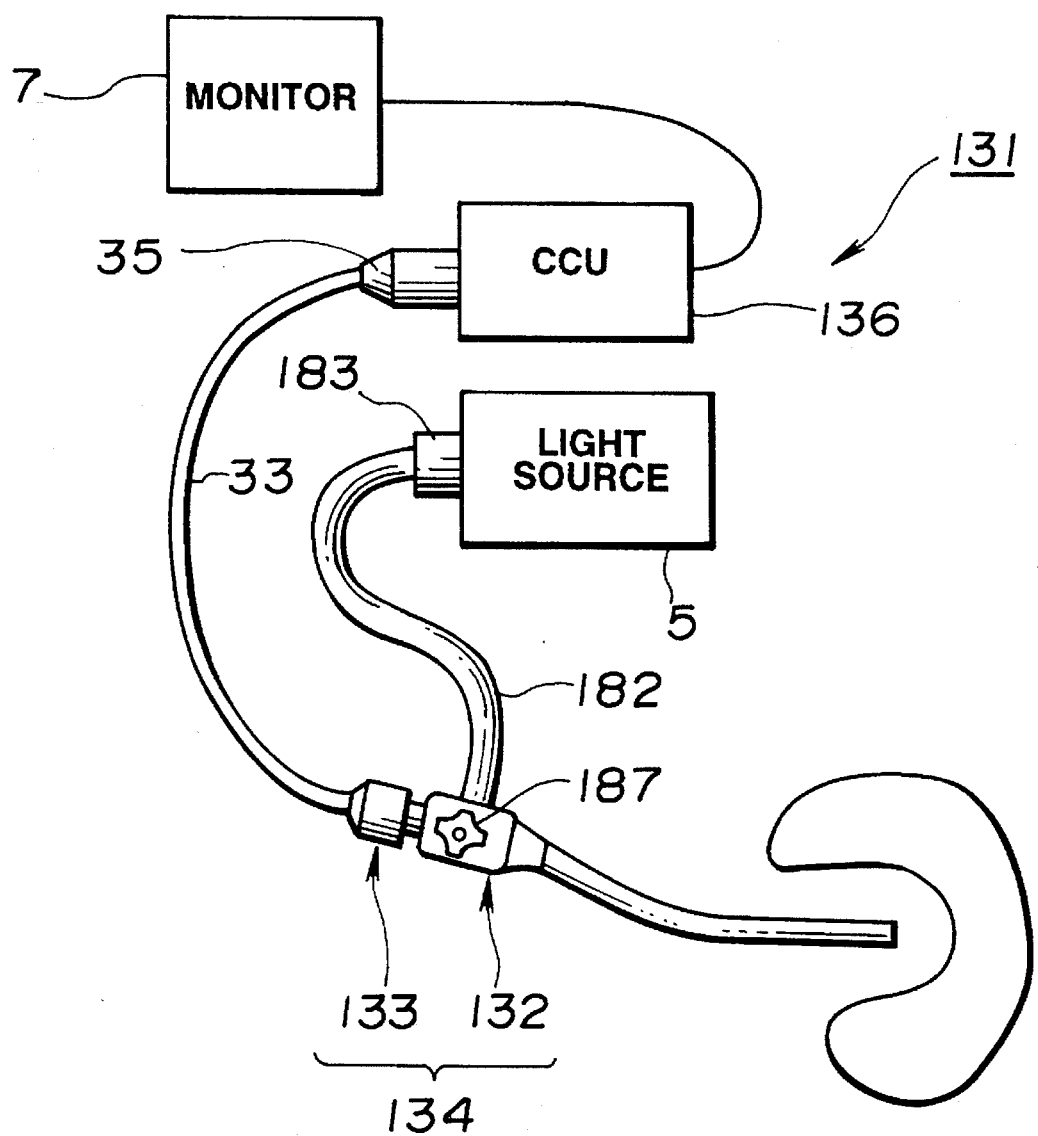
FIGS. 12 to 14 relate to a fourth embodiment of the invention, where.

FIG. 12 shows an endoscope apparatus 131 according to a fourth embodiment of the invention. The endoscope apparatus 131 uses an endoscope 134 on which a TV camera is exterior-mounted, which is formed by a flexible endoscope 132 and a TV camera 133 which is mounted on the flexible endoscope 132.

Figure 13:
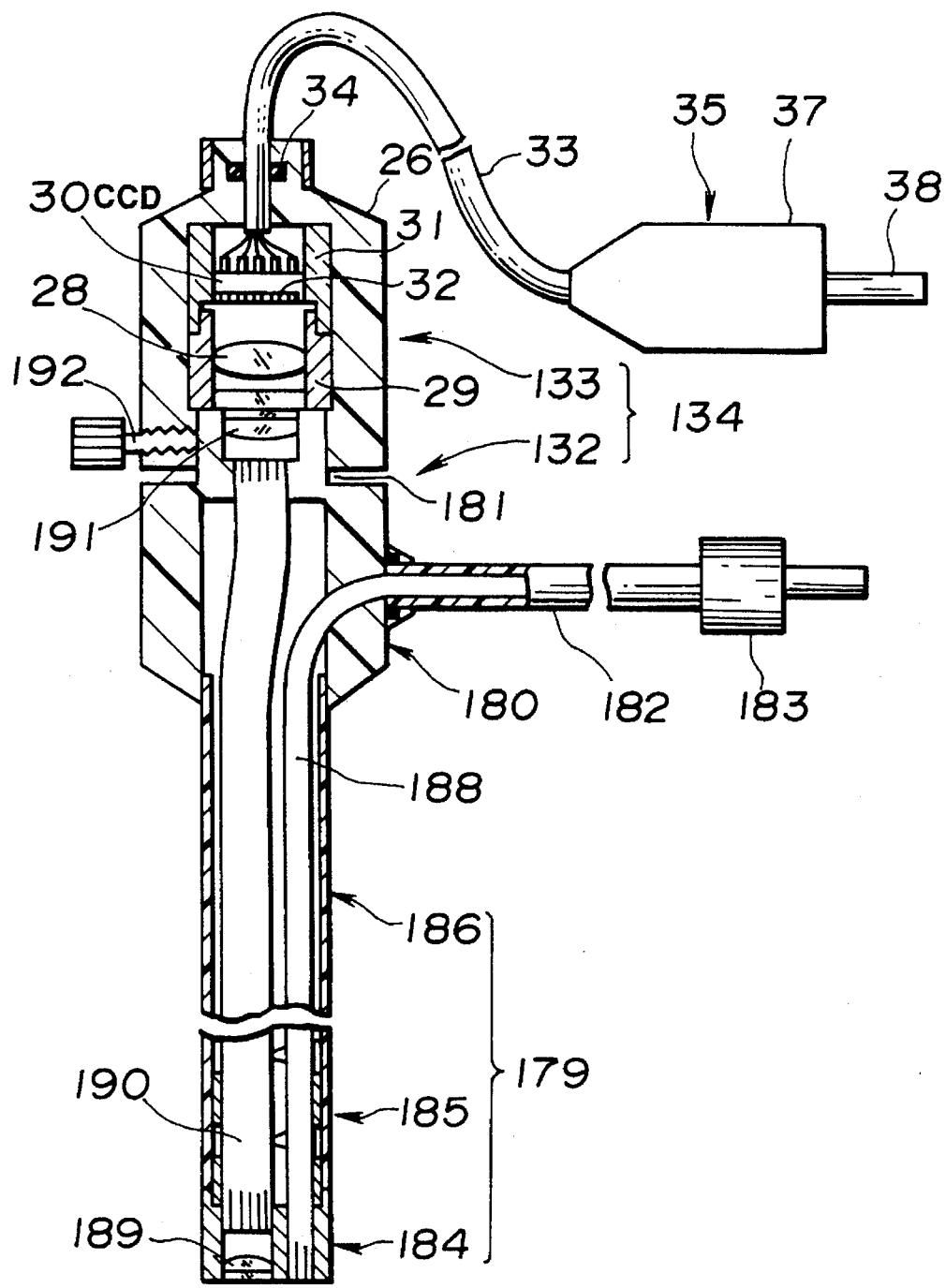

FIG. 13 shows a structure of the endoscope 134 on which the TV camera is exterior-mounted. The flexible endoscope 132 is provided with an operating section 180 at a proximal end of an inserting section 179 which has flexibility. An ocular portion 181 is provided at a rearward end of the operating section 180. A resilient or elastic light guide cable 182 extends from a side surface of the operating section 180. A light guide connector 183 is provided at a distal end of the light guide cable 182.

The inserting section 179 is formed by a rigid forward end 184, a curvature portion 185 formed adjacent to the forward end 184, and an elastic tube 186 having elasticity extending from the rearward end of the curvature portion 185 to a forward end of the operating section 180. The curvature portion 185 is capable of being curved by rotational operation of a curvature operating knob 187 (refer to FIG. 12) which is provided on the operating section 180.

The inserting section 179 is covered with an elastic tube. A light guide 188 is inserted into the tube. The light guide 188 is inserted into the light guide cable 182 from the operating section 180 so that the light guide connector 183 can be detachably mounted on a light source unit 5. Illuminating light transmitted by the light guide 188 is projected forwardly from the forward end face of the light guide 188 which is fixedly mounted on an illuminating window at the forward end 184. The forward end 184 is provided with an observing window, adjacent to the illuminating window, which is closed by a cover glass material. An objective lens 189 is mounted within the observing window.

A forward end surface of an image guide 190 is arranged at a focal surface (an imaging position) of the objective lens 189 so that an optical image of a subject is formed on the forward end surface. The image guide 190 is inserted into the inserting section 179. The image guide 190 has a rearward end surface which extends to the neighborhood of the ocular portion 181.

The optical image on the forward end surface is transmitted to the rearward end surface by the image guide 190. An ocular lens 191 is arranged on the ocular portion 181 in opposed relation to the rearward end surface thereof. Thus, it is possible to observe, in enlargement, the optical image which is transmitted from the ocular window closed by the cover glass material. The flexible endoscope 132 has a liquid-tight and gas-tight structure, and is dipped within cleaning and disinfection liquid and is disinfected by cleaning liquid after the flexible endoscope 132 has been used for endoscope inspection.

The TV camera 133 is mounted on the ocular portion 181 of the flexible endoscope 132 by a fixing screw 192. The TV camera 133 is substantially the same in arrangement as the TV camera 3 illustrated in FIG. 3. Identical reference numerals are applied to identical elements (members), and the description thereof will be omitted. An electric connector 35 which is mounted on a distal end of a signal transmitting cable 33 of the TV camera 133 can be detachably mounted on a CCU 136.

Since, in the present embodiment, the flexible endoscope 132 is used, for example, where various internal organs, such as the stomach, are inspected with the endoscope, the inserting section 179 is inserted form a cavum oris, and the internal organs illuminated by illuminating light projecting from an illuminating window in the forward end 184 are focused onto a forward end surface of the image guide 190 by the objective lens 189 which is mounted on the observing window.

The function of displaying, in color, the image transmitted by the image guide 190, by a color monitor 7 is the same as that of the first embodiment.

Figure 14:
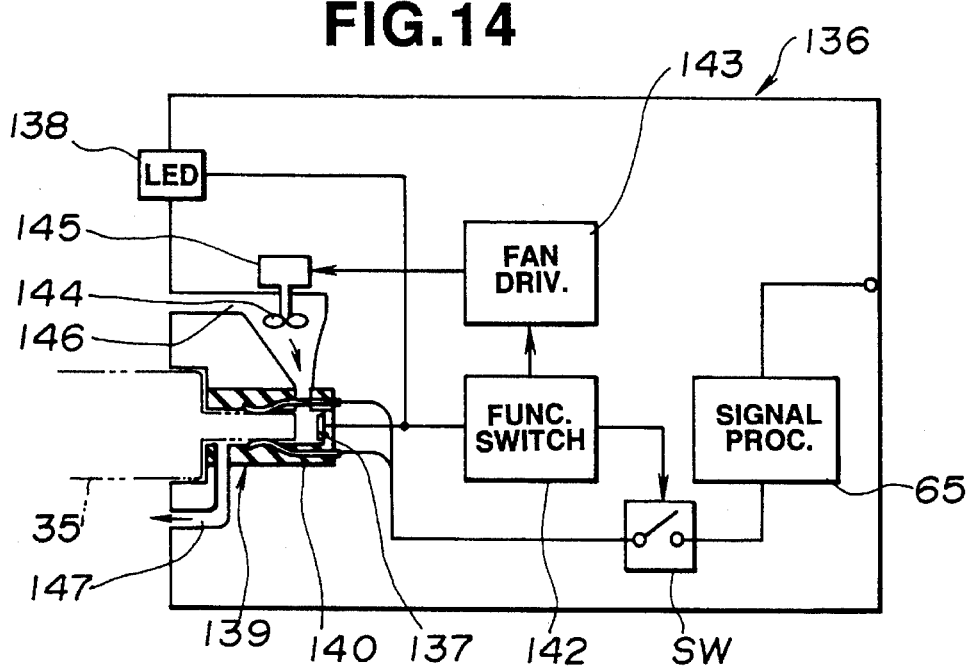

An arrangement of the CCU 136 in the present embodiment is illustrated in FIG. 14. The present embodiment has a humidity detecting sensor 137 for detecting humidity, similarly to the third embodiment. During a time period in which the humidity is detected, a user is notified that there is humidity by an LED 138, for example.

When the electrical connector 35 is inserted into an electrical connector receptacle 139 of the CCU 136, an electrical contact 43 of the electrical connector 35 is in contact with an electrical contact 140 of the electrical connector receptacle 139 so that the exterior-mounted camera 133 is electrically connected to the CCU 136. The humidity sensor 137 is received within a recess in the electrical connector receptacle 139, to detect presence and absence of humidity and moisture (or presence and absence of wetting) due to the electrical connector 35.

A warning unit such as the LED 138, a buzzer, etc. is electrically connected to the humidity sensor 137. When the humidity sensor 137 detects moisture on the electrical connector 35 or a degree of humidity having a possibility of producing a short-circuit the LED 138 emits light to issue a warning. A function switching portion 142 connected to the humidity sensor 137 activates a fan drive portion 143 to rotate a motor 145 which has a fan 144 mounted thereon.

In the case, the condition is as follows. That is, the function switching portion 142 turns OFF a switch SW, and the electrical contact 140 is maintained under a cut-off condition in which the electrical contact 140 is not electrically connected to a signal processing circuit 65. Even if locations between a plurality of electrical contacts 140 and 140 are short-circuited, current does not flow. Under this condition, since signal processing with respect to the CCD does not occur, observation due to a color monitor 7 is impossible.

The fan 144 arranged within a gas-feeding passage 146 feeds air into the recess in the electrical connector receptacle 139 by rotation of the motor 145, to evaporate the moisture on the electrical contact 43, to thereby exhaust the air from a discharge passage 147. When the humidity detected by the humidity sensor 137 is sufficiently lowered, the LED 138 is turned off by an output from the humidity sensor 137. The function switching portion 142 turns OFF (halt in operation) the fan drive portion 143, and turns ON the switch SW to connect the electrical contact 140 and the signal processing circuit 65.

Under this condition, the signal processing circuit 65 is electrically connected to the CCD. An image processed signal is displayed on the color monitor 7.

Moreover, in a case where moisture on the electrical connector 35 is not detected by the humidity sensor 137, the function switching portion 142 switches the switch SW to turning-ON to bring the signal processing circuit 65, which becomes the main function, to a normal operating condition. Thus, observation due to the color monitor 7 becomes possible.

In the present embodiment, the LED 138 is turned on during the period of time in which drying processing is performed. Thus, it is possible for the user to view the drying processing.

Figure 15:
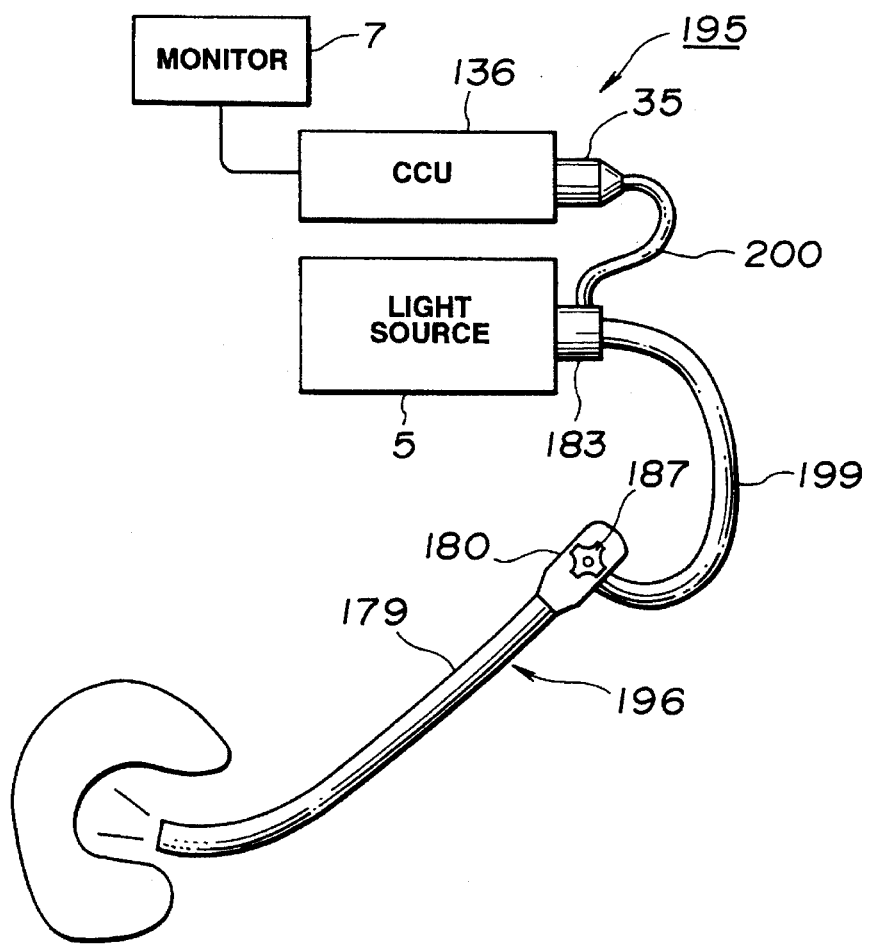
FIGS. 15 and 16 relate to a modification of the fourth embodiment, where.

FIG. 15 shows an endoscope apparatus 195 according to a modification of the fourth embodiment. The endoscope apparatus 195 uses a flexible electronic endoscope 196 in place of the TV-camera exterior-mounted endoscope 134 in which the TV camera 133 is mounted on the flexible endoscope 132, in the endoscope apparatus 131 according to the third embodiment.

Figure 16:
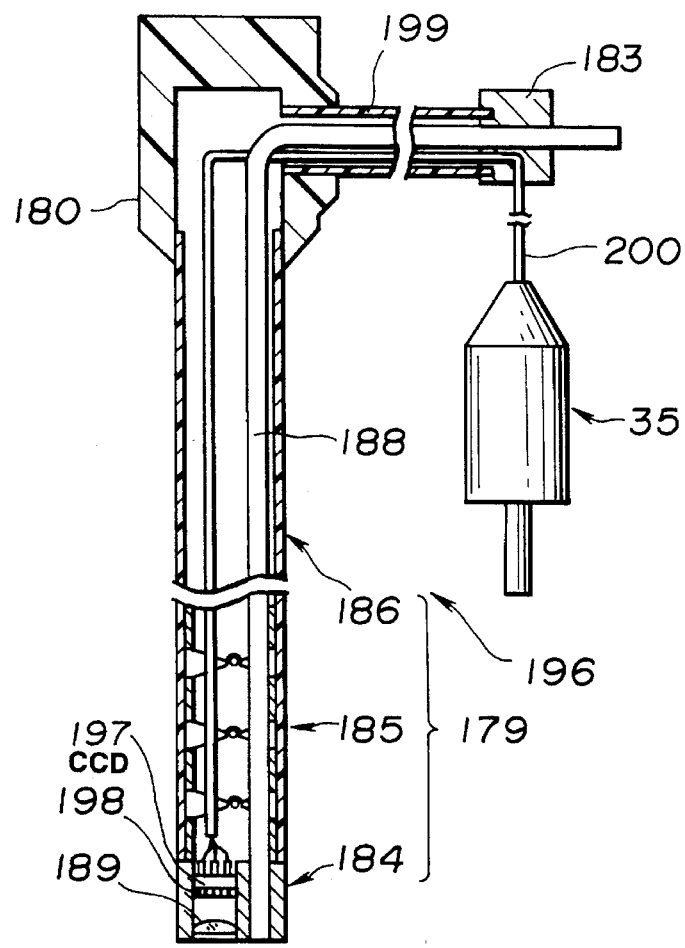

A structure of the electronic endoscope 196 is shown in FIG. 16. The electronic endoscope 196 is arranged such that, in the flexible endoscope 132 illustrated in FIG. 13, a CCD 197 is arranged at a focal surface of an objective lens 189. A color separation filter 198 is mounted on an image pickup surface of the CCD 197.

A signal cable connected to the CCD 197 is inserted into a flexible inserting section 179, and is inserted into a universal cable 199 extending from an operating section 180, together with a light guide 188. The universal cable 199 has a distal end thereof on which a light guide connector 183 is provided. Thus, the light guide connector 183 is detachably mounted on a light source unit 5.

Furthermore, a cord 200 into which the signal cable is inserted extends from a side portion of the light guide connector 183. The cord 200 has a distal end thereof on which an electrical connector 35 is provided. The electrical connector 35 can be detachably mounted on the CCU 136. The electronic endoscope 196 also has a liquid-tight and gas-tight structure so that the electronic endoscope 196 can be dipped within a disinfection liquid to be disinfected.

The other arrangements are similar to that described with reference to the third embodiment, and the description thereof will be omitted. Function or operation of the present modification are substantially the same as those of the third embodiment.

Figure 17:
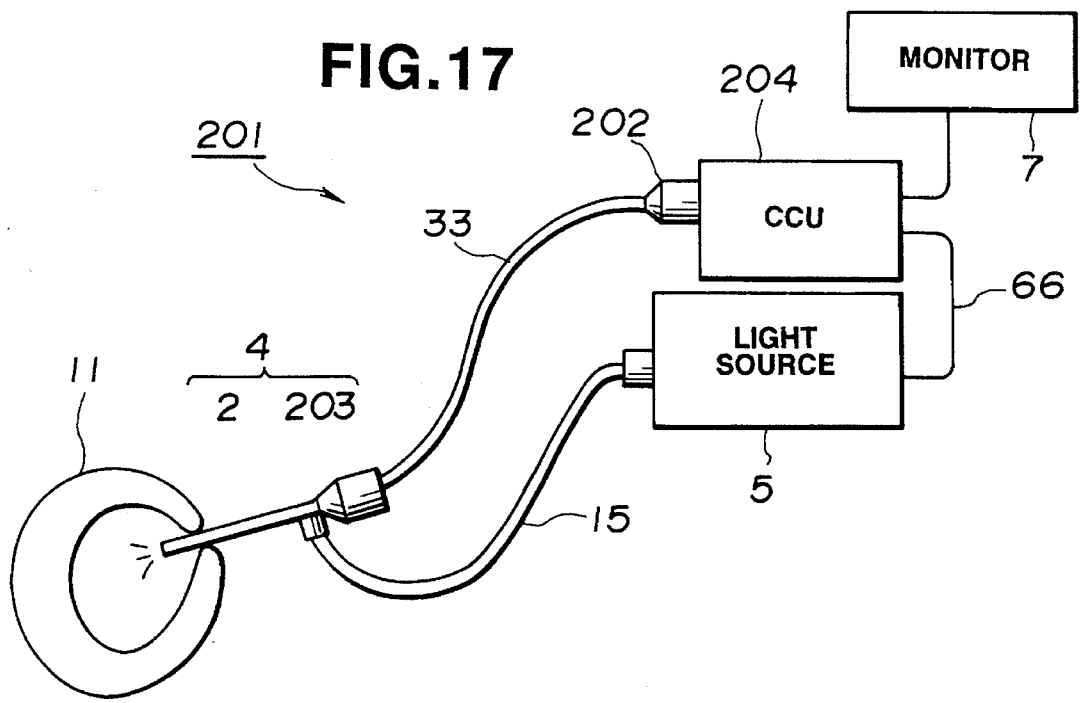

FIG. 17 shows an endoscope apparatus 201 according to a fifth embodiment of the invention. The endoscope apparatus 201 comprises a TV camera 203 having an electrical connector 202, for example, which is different from the electrical connector 35 in the second embodiment, and a CCU 204 having dry processing means, different from the CCU 70. The rest of the embodiment is similar in arrangement to the second embodiment.

Figure 18A:
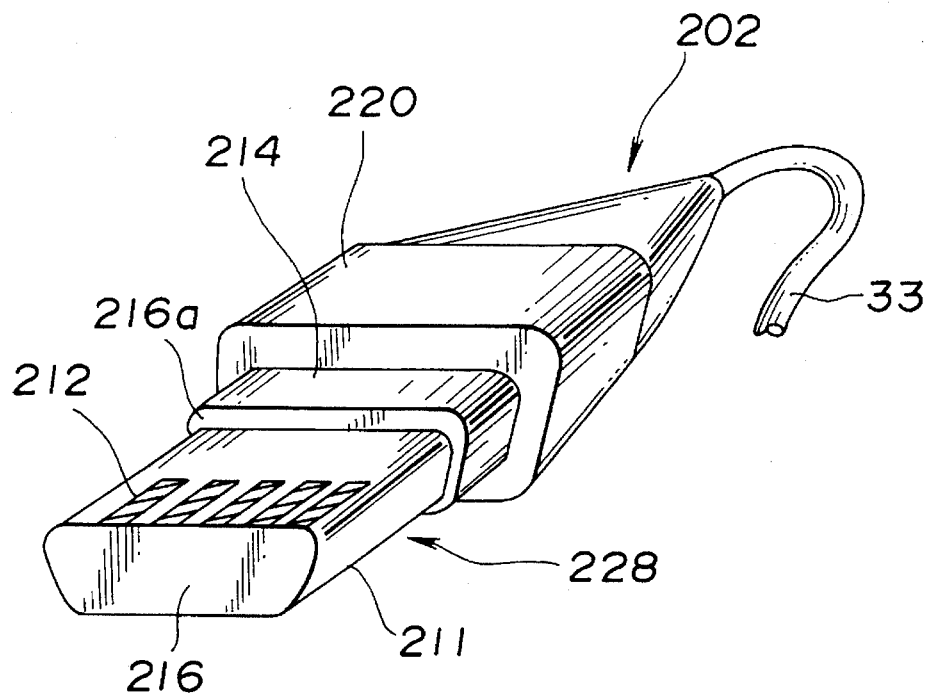
FIGS. 18a and 18b are perspective views showing an outer configuration and an interior structure of an electrical connector, respectively.
Figure 18B:
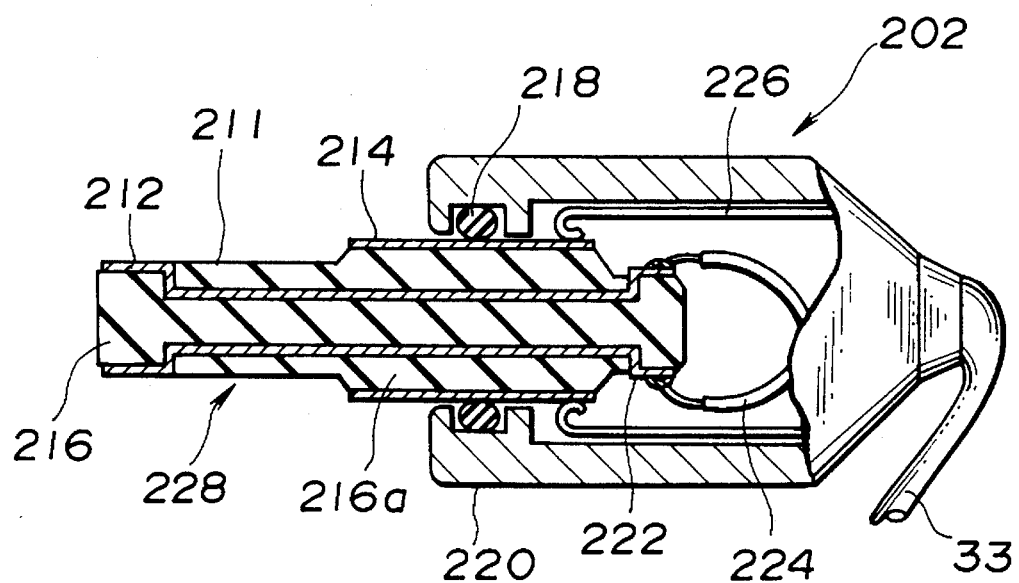

FIGS. 18*a* and 18*b* show a structure of the electrical connector 202. The electrical connector 202 which is provided at a distal end of a cable 33 of the TV camera 203 has a base 211 which is provided, in plane, with a plurality of contact patterns (electrical contacts) 212 and 222 on both surfaces of a plate-like electrical insulating element 216. A shield pattern 214 which serves as a contact of a shield portion on the side of the electrical connector for isolating or interrupting noises is provided, in plane, on an outer periphery of the base 211, whereby an electrical connector body 228 thereof is formed.

The electrical connector 228 is liquid-tightly connected to an electrical connector cover 220 through a sealing element 218, whereby the electrical connector 220 is formed.

The electrical insulating element 216 has a flat or planar configuration, and the plurality of contact patterns 212 are formed at a forward end of the base 219 which has the planar surface. The contact patterns 212 are in contact with an electrical contact which is provided on the electrical connector receptacle (refer to FIG. 19) on the side of the CCU 204, whereby the CCU 204 is electrically connected to the TV camera 203.

Moreover, the contact pattern 222 is similarly formed on a rearward end of the base 219. The contact patterns 212 and the contact pattern 222 are arranged such that parts thereof corresponding to each other are conducted to each other through the interior of the electric insulating element 216.

Furthermore, the electrical insulating element 216 is arranged such that a portion on the way between the contact patterns 212 and the contact pattern 222 is formed into a wall thickened portion 216*a* of a planar configuration having a planar surface further raised at a single step. The shield pattern 214 is provided which has an extremely smoothed surface over the entire periphery of the surface of the wall thickened portion 216*a*.

The electrical connector cover 220 and the electrical connector body 228 are liquid-tightly connected to each other with a surface of the shield pattern 214 serving as a sealing surface. That is, the electrical connector body 228 and the electric connector cover 220 are brought to a liquid-tight structure by the fact that the sealing element 218 is interposed between the surface of the shield pattern 214 and an inner surface of the forward end of the electrical connector cover 228.

Further, in the structure, parts on the side of the contact pattern 222 and the shield pattern 214 are arranged within the electrical contact cover 220. Various kinds or types of signal lines 224 which are introduced into the electrical connector cover 220 through the cable 33 are soldered to the contact pattern 222 which is located within the electrical connector cover 220. A shield element 226 having a proximal end thereof grounded has a forward end thereof which is introduced into the electrical connector cover 220 through the cable 33.

The forward end of the shield element 226 is in contact with a part of the shield pattern 214 on the side of a rearward end thereof, which is located within the electrical contact cover 220, whereby the shield element 226 forms a shield portion on the side of the electrical connector together with the shield pattern 214. In this case, if the electrical connector 202 is fitted into the electrical connector receptacle of the CCU 204, whereby the shield pattern 214 is in perfect contact with the shield portion on the side of the CCU 204, it is possible to cut off noise from the outside, and it is possible to suppress noise from the side of the exterior-mounted camera 203 to the side of the CCU 204.

Accordingly, with the endoscope apparatus 201 having the arrangement described above, since the electrical connector 202 is formed into a liquid-tight structure with the surface of the shield pattern 214 which forms an extremely smooth surface over the entire periphery serving as a sealing surface, it is possible to provide a liquid-tight condition which is extremely high in reliability.

Moreover, since the electrical connector body is not formed by molding, also including the sealing surface, but the shield pattern 214 serving as the sealing surface is formed on the outer surface of the base 211 consisting of the electrical insulating element 216, the manufacturing yield is superior, making it easier to repair the connector portion. Furthermore, since the contact patterns 212 serving as the electrical contact are provided in the form of a surface or plane on the base 211 which has a planar surface, even if liquid adheres to the base 211, it is easy to wipe off. Accordingly, no residue of the liquid remains. Thus, it is possible to prevent short-circuiting of the electrical contact.

Figure 19A:
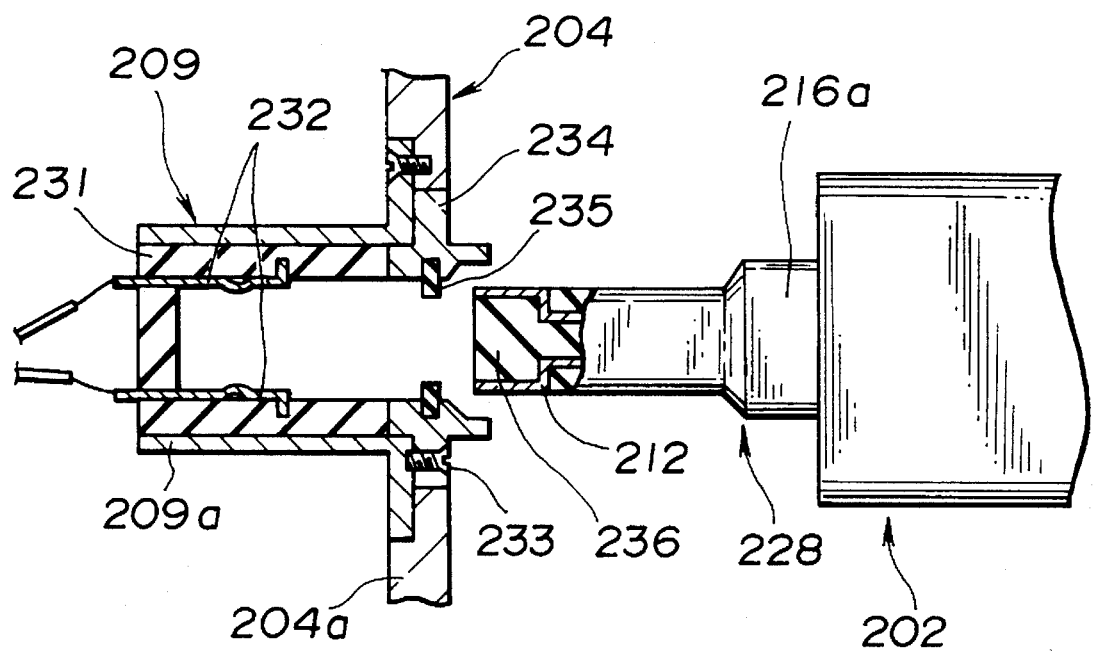

FIG. 19*a* shows a structure of the connector receptacle 209 in the CCU 204. A plate-like bore is formed in a front surface of the CCU 204. A metallic flat armor frame (connector shell) in the form of a ring 209*a* of the electrical connector receptacle 209 to which the electrical connector 202 is capable of being connected is mounted on a metallic CCU frame 204*a* by screws.

An insulator 231 which is a flat ring configuration and which is provided with a receiving portion which is capable of receiving the base 211 of the electrical connector 202 is mounted within the armor frame 209*a*. A plurality of electrical contacts 232 are mounted on the inner sides deep within the insulator 231. The electrical contacts 232 are connected to a signal processing circuit (not shown) through a signal line.

A moisture absorption element 235 is mounted at an entrance of the electrical connector receptacle 209 which serves as a proximal end of the armor frame 209*a*, through a metallic moisture-absorption-element receiving element 234 which is mounted on the armor frame 209*a* by screws 233. The moisture absorption element 235 has an outer peripheral side of an elastic element having a moisture absorption function, such as sponge, in the form of a ring is received, by force fitting into a recess or a groove which is provided in an inner wall surface of the moisture-absorption-element receiving element 234 in the form of a flat ring. An inner peripheral side of the moisture absorption element 235 projects inwardly.

When operation is performed to insert a portion of the base 211 of the electrical connector 202 into a connector connecting receiving portion of the electrical connector receptacle 209 which is provided with the moisture absorption element 235, the side of the forward end projecting inwardly of the moisture absorption element 235 is in contact with the flat surface of the base 211 so as to urge the same. Accordingly, when insertion occurs toward the deep portion of the receiving portion, even if the moisture 236 (refer to FIG. 19*a*) adheres to the surface of the base 211, the moisture 236 is absorbed when contact is performed with respect to the moisture absorption element 235 so that the moisture 236 is removed from the surface of the base 211.

Figure 19B:
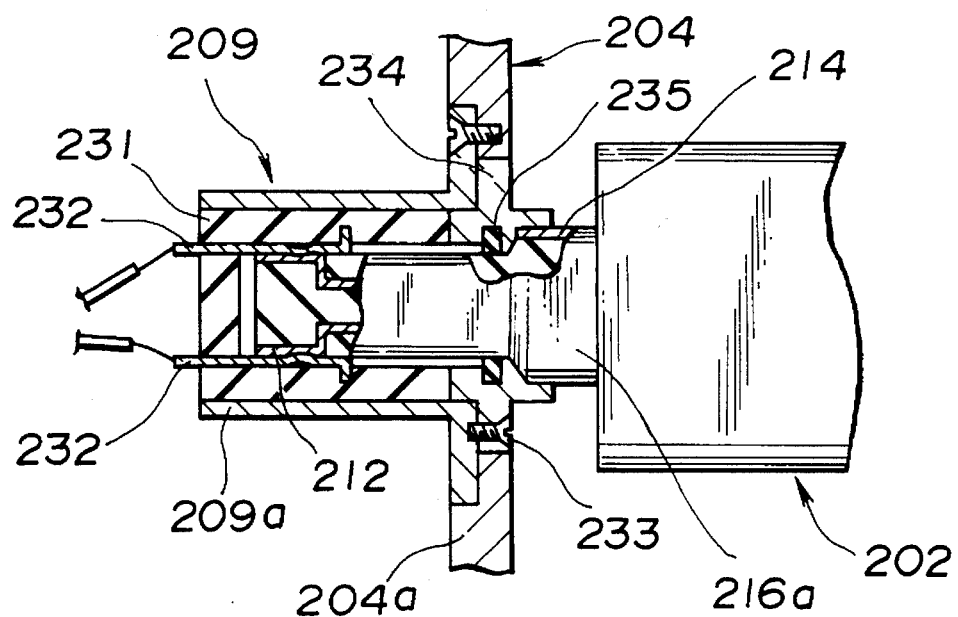

As shown in FIG. 19b, under a condition that the electrical connector 202 is mounted on the electrical connector receptacle 209, contact patterns 212 which are exposed to the surface on the side of the forward end of the base 211 are in contact with the electrical contacts 232 of the electrical connector receptacle 209.

Accordingly, the CCU 204 and the TV camera 203 are electrically connected to each other. Furthermore, under the mounting or fitting condition, since a shield pattern 214 of a wall thickened portion 216a is in contact with a projection of the moisture-absorption-element receptacle element 234, the shield pattern 214 is conducted to the armor frame 209a through the moisture-absorption-element receptacle element 234, to retain shield function.

According to the present embodiment, by mounting the electrical connector 202 on the electrical connector receptacle 209, the moisture remaining on the surface of the base 211 of the electrical connector 202 can be removed by the moisture absorption element 235, thereby preventing short-circuits.

In a case where the moisture absorption element 235 is humidified after use, the moisture absorption element 235 is taken out from the recess in the moisture-absorption-receptacle element 234, and is replaced by a new moisture absorption element or another moisture absorption element. Alternatively, the moisture absorption element 235 may be replaced by the screw 233, including also the moisture-absorption-element receptacle element 234.

Figure 20:
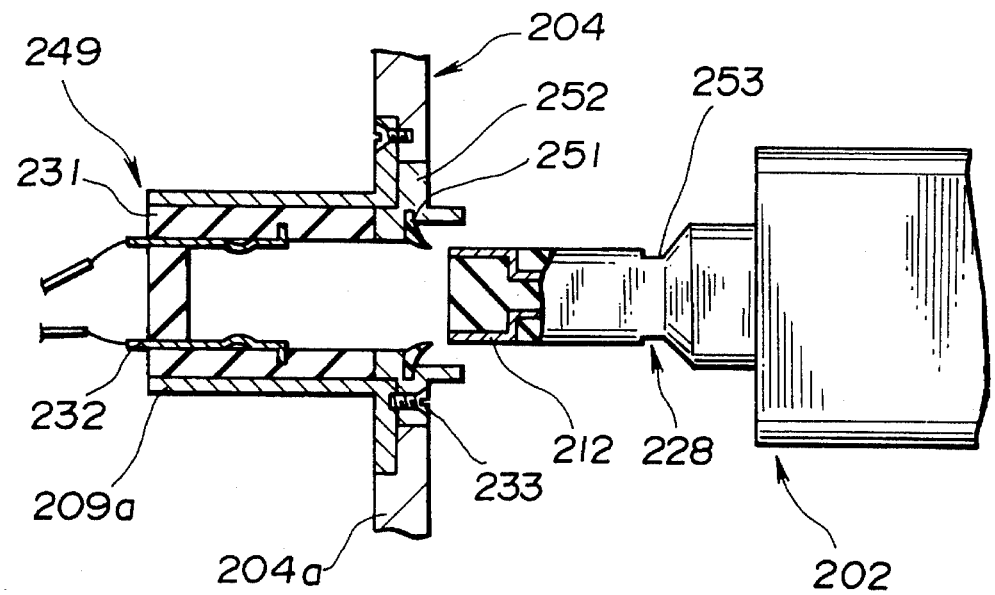
FIG. 20 is a cross-sectional view showing a structure in the vicinity of an electrical connector in a first modification of the fifth embodiment.

FIG. 20 shows the periphery of an electrical connector receptacle 249 in a first modification of the fifth embodiment. The modification is arranged such that a wiper 251 for wiping out liquid such as moisture is mounted through a wiper receptacle element 252 in place of the moisture absorption element 235 in FIG. 19a. The wiper 251 has a forward end thereof which is in close or intimate contact with the base surface of the electrical connector 202. Wiped liquid is reserved in a receptacle groove 253 on the base rearward side of the electrical connector 202. Since the receptacle groove 253 forms an electrical insulating element part on the rearward side more than a portion to which the contact pattern 212 is exposed, no short-circuiting is generated. The other arrangements are the same as in the fifth embodiment. A groove for reserving the wiped liquid may be provided on the side of the electrical receptacle 249.

Figure 21:
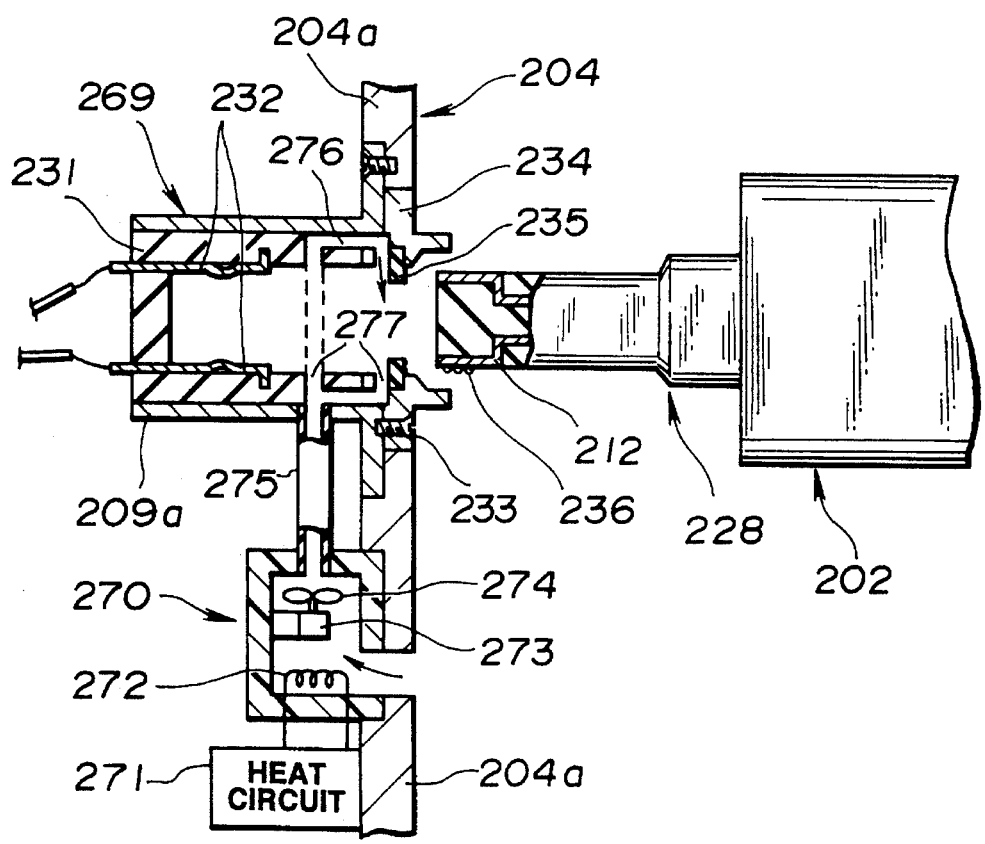
FIG. 21 is a cross-sectional view showing a structure in the vicinity of an electrical connector receptacle in a second modification of the fifth embodiment.

FIG. 21 shows a structure in the vicinity of an electrical connector receptacle 269 in a second modification of the fifth embodiment.

The modification is arranged such that, in FIG. 19a, for example, a gas-feeding mechanism 270 is further provided to dry a moisture absorption element 235, and to dry the inserted electrical connector 202.

A room which opens to the outside is provided below an electrical connector receptacle 269. A heating wire 272 connected to a heating circuit 271 is received in the room. Air heated by the heating wire 272 is sent out from openings 277 in an inner wall surface of the insulator 231, inwardly of the inner wall surface through a tube 275 connected to an opening provided upwardly and a passage 276 connected to the tube 275 and located within the insulator 231, by a fan 274 which is mounted on a motor 273.

The openings 277 are provided in the vicinity of the moisture absorption element 235 which is provided at an entrance, to evaporate liquid of the moisture absorption element 235 to dry the same, and to evaporate the liquid of the electrical connector 202 which is inserted into the electrical connector receptacle 269.

According to the present modification, since, even if the moisture absorption element 235 is moistened, the moisture absorption element 235 is dried in a short period of time by heated air. Thus, the liquid removing function with respect to the connected electrical connector 202 can be maintained, unless the moisture absorption element 235 is frequently replaced. In the present modification, the heated air is used to perform drying, but air which is not heated may be used.

Moreover, a gas-feeding mechanism may be provided with respect to the first modification illustrated in FIG. 20.

Figure 22:
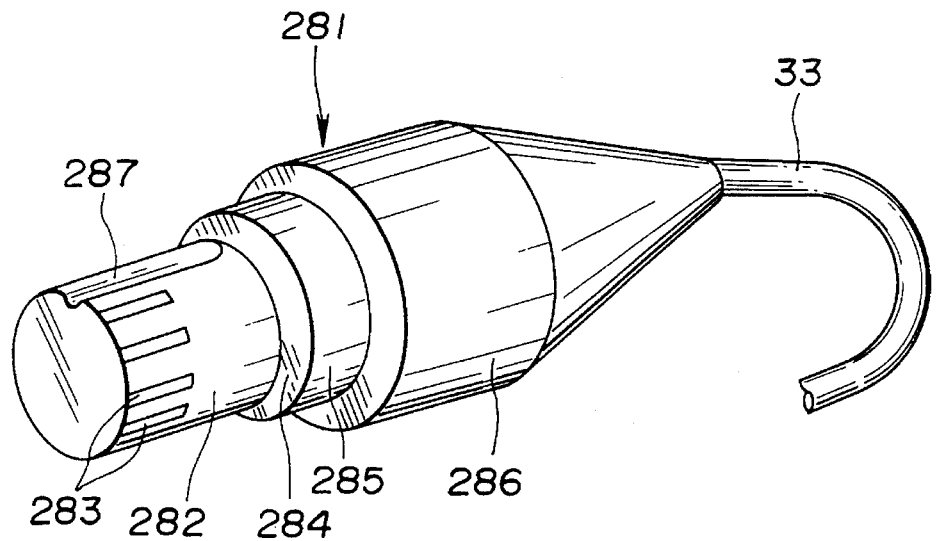
FIG. 22 is a perspective view showing an outer configuration of an electrical connector in a third modification of the fifth embodiment.

FIG. 22 shows an electrical connector 281 in a third modification of the fifth embodiment. The electrical connector 202 of the fifth embodiment has a flat plate configuration as shown in FIG. 18a, whereas the electrical connector 281 of the modification has a columnar configuration. That is, a plurality of contact patterns 283 are provided to be exposed to a surface of a base 282 formed by an electrical insulating element having a columnar configuration on the side of a forward end of the base 282.

The exposed contact patterns 283 are flush with a columnar outer peripheral surface of the base 282. A ring-like shield pattern 285 is formed on a diameter thickened portion 284 rearwardly thereof. A cover 286 is provided rearwardly of the shield pattern 285.

Further, a cut-out 287, for example, is provided at a single location on the outer peripheral surface for the purpose of positioning. A projection is provided at a location corresponding to the cut-out 287 on the side of an electrical connector receptacle (not shown) which is provided with a columnar receiving portion and to which the electrical connector 281 is connectable. Thus, a structure is formed in which connection cannot be made unless a condition is such a condition under which the cut-out 287 is positioned to the projection. The other arrangements are similar to that of the fourth embodiment.

A sixth embodiment of the invention in which a liquid removal mechanism is provided on the side of the electrical connector will next be described with reference to FIG. 23. An electrical connector 301 is arranged such that, in the electrical connector 35 illustrated, for example, in FIG. 4a, an air channel is provided in a connector body 37, and air fed from air-feeding means is discharged from the side of a forward end surface, to remove liquid in the vicinity of an electrical contact 43. For this reason, the same or similar reference numerals are applied to elements the same or similar to those illustrated in FIG. 4.

Figure 23:
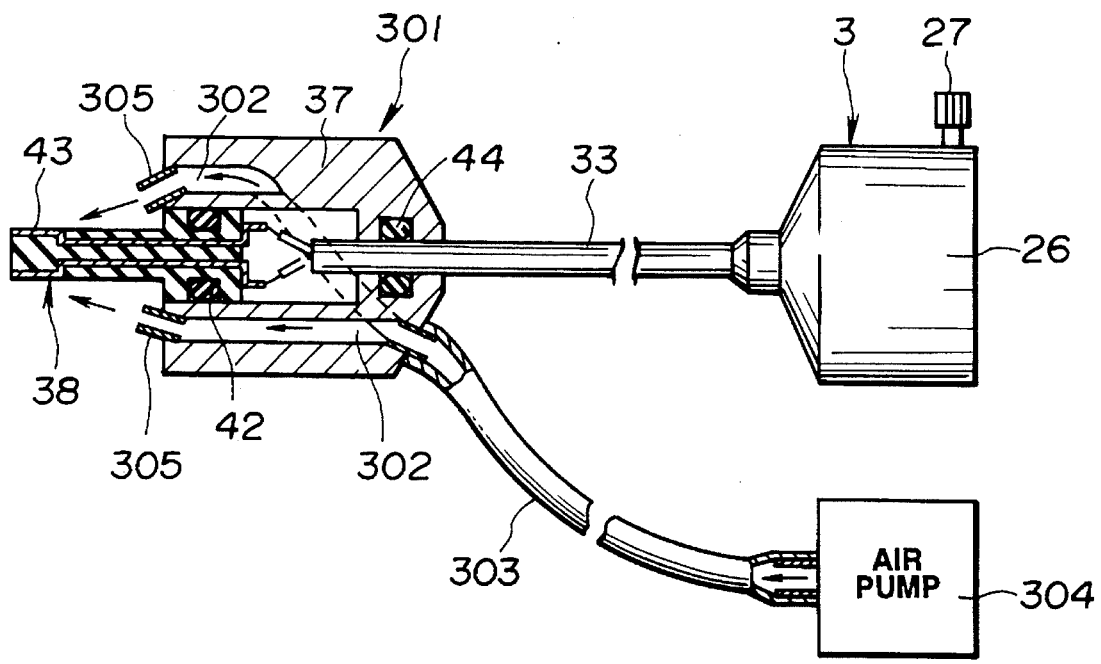
FIG. 23 is a cross-sectional view showing an electrical connector according to a sixth embodiment of the invention.

As shown in FIG. 23, the electrical connector 301 is mounted on a distal end of a cable 33 into which a signal line connected to the CCD (refer to FIG. 3) received within a TV camera 3 is inserted.

Similarly to FIG. 4a, a connector portion 38 has a proximal end 40 thereof which is fitted into the recess in a connector body 37 of the electrical connector 301, and is fixed by screws (not shown). The electrical contact 43 is embedded in an insulator which forms the connector portion 38. The electrical contact 43 has a forward end thereof which is exposed, and a rearward end thereof which is connected to the signal line.

In the present embodiment, a pair of flat air channels 302 and 302 are provided within the connector body 37, on both sides of the connector portion 37. The sides of the air channels 302 and 302 adjacent to proximal ends thereof are joined together or meet together to reach the base.

A tube 303 has one end thereof which is connected to the base. The other end of the tube 303 is connected to an air pump 304. Air from the air pump 304 is fed into the air channel 302 from the base by the rubber hose 303, and is discharged from a discharging nozzle 305 which is mounted on an opening in a forward end surface. By the discharged air, the liquid remaining on the side of the forward end of the connector portion 38 is removed and is evaporated. In the present embodiment, the electrical connector 301 is such that a connecting portion between the signal line and the electrical contact 43 has a liquid-tight structure similar to the first embodiment.

In the arrangement, in a case where a small quantity of liquid adheres to the electrical connector 301, the rubber hose 303 connected to the air pump 304 is first connected to the base 81 of the electrical connector 301. When a switch (not shown) of the air pump 304 is turned ON, air from the air pump 304 passes through the rubber hose 303 and the air channels 302 and is discharged toward the side of the electrical contact 43 from the discharge port. Thus, the remaining liquid which is adhered to the vicinity of the electrical contact 43 is dried and is removed.

Figure 24:
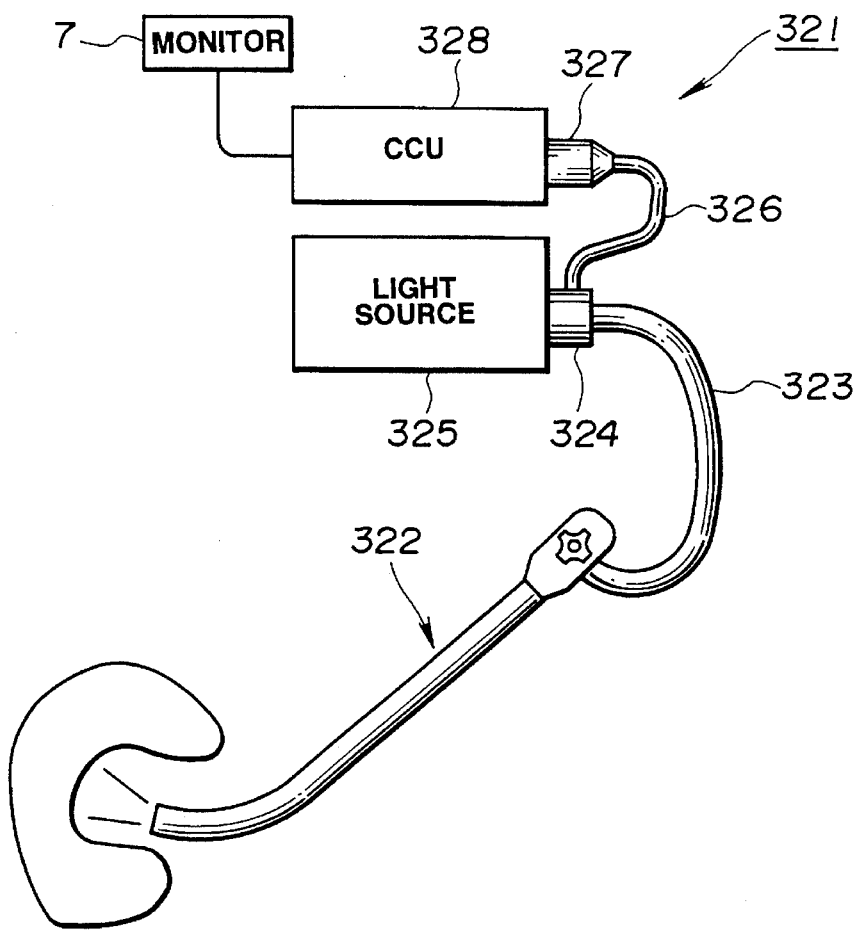

FIG. 24 shows an endoscope apparatus 321 according to a seventh embodiment of the invention. The embodiment forms a mechanism which utilizes heat generated by a light source unit similar to the first embodiment to remove moisture, with respect to the endoscope apparatus 195 illustrated in, for example, FIG. 15.

The endoscope apparatus 321 is arranged as follows. Specifically, a light guide connector 324 which is provided at a distal end of a universal cable 323 of an electronic endoscope 322 of an electronic endoscope 322 is detachably mounted on a light source unit 325, and an electrical connector 327 which is provided at a distal end of a cable 326 extending from the light guide connector 324 is detachable to a CCU 328.

Figure 25:
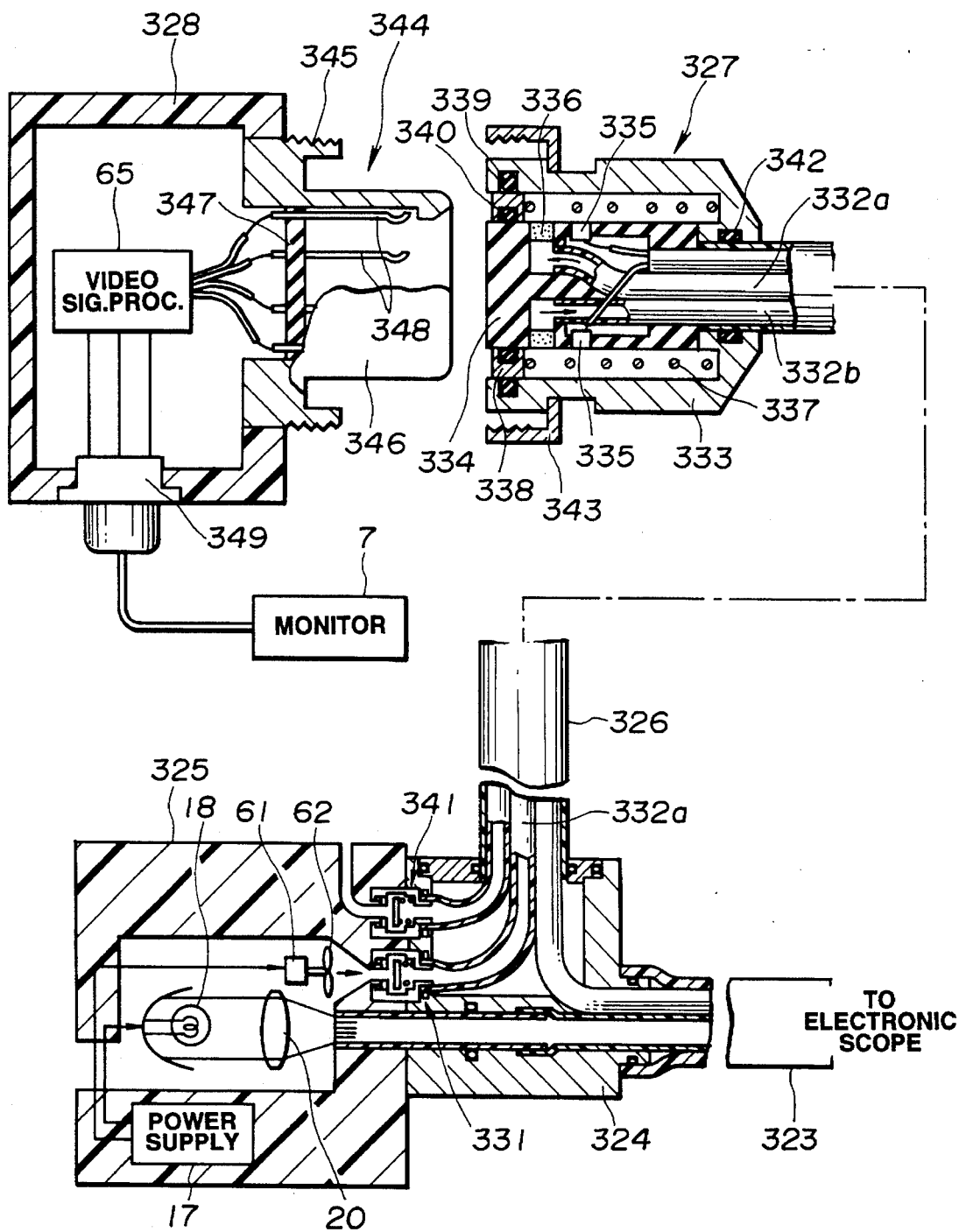

As shown in FIG. 25, the light source unit 325 converges illuminating light from a lamp 18 by a condenser lens 20 to irradiate the condensed light toward an end surface of the light guide connector 324. A fan 62 rotated by a motor 61 is arranged above the condenser lens 20, to feed heated air into the electrical connector 327 through a gas-feeding tube 322a which is provided with a gas-feeding connector 331 mounted on an opening thereof.

The electrical connector 327 is such that a substantially cylindrical connecting element 334 formed of an insulator is concentrically arranged within a cylindrical connector body 333, a plurality of electrical contacts 335 of embedded type are arranged on an outer peripheral surface on the side of the connecting element 334, and heads thereof are exposed to the outer peripheral surface of the connecting element 334. The electrical contacts 335 are connected to a signal line within the cable 326 by soldering.

Furthermore, a sponge 336 serving as liquid removing means for absorbing liquid to remove the same is arranged on the outer peripheral surface of the side portion on the forward side (end surface of the connecting element 334) more than the electrical contact 335 in the connecting element 334. The sponge 336 is formed into, for example, a ring-like configuration, and an outer peripheral surface thereof is exposed to the outer peripheral surface of the connecting element 334.

A moving element 338 in the form of a ring which is biased axially by a spring 337 is interposed between an inner peripheral surface of the connector body 333 and an outer peripheral surface of the connecting element 334.

A sealing element 339 such as an O-ring is received in a groove in an inner peripheral surface of a forward end of the connector body 333, and a sealing element 340 such as an O-ring is received in a groove in an inner peripheral surface of the moving element 338. Thus, the moving element 338 can be moved axially under a waterproof condition.

Further, a gas-feeding tube 332a which is inserted into the cable 326 has an end thereof which is fixedly mounted on the connecting element 334 at an inner side of the sponge 336, and which opens within a ring-like space in which the sponge 336 is received.

The heated air which is fed from the opening is supplied into the space, to evaporate moisture of the sponge 336. A discharging tube 332b has an end thereof which opens into the space. The other end of the discharging tube 332b which is inserted into the cable 326 is mounted on the opening in the light source unit 325 by a discharging connector 341. The opening communicates with the outside to discharge the air fed by the discharging tube 332b to the outside.

Liquid tightness is maintained by a sealing element 342 on the side of the proximal end of the electrical connector 327. Moreover, a liquid tightness on the side of the light guide connector 324 is also secured by the sealing element.

A fixing ring 343 is provided on the outside of the connector body 333 of the electrical connector 327. The fixing ring 343 is threadedly engaged with a threaded portion 345 of an electrical connector receptacle 344 of the CCU 328 to enable the electrical connector 327 to be connected thereto.

A plurality of electrical contact receptacles 348 are provided in projection on a disc-like insulator 347 on the side of a proximal end of the proximal of the cylindrical connector receptacle body 346 of the electrical connector receptacle 344 so as to extend therethrough.

Proximal ends of the respective electrical contact receptacles 348 are connected to a signal processing circuit 65 through signal lines. An image signal which is outputted from the signal processing circuit 65 is inputted into a monitor 7 through a connector which is connected to a connector receptacle 349. The monitor 7 displays an endoscope image.

A cylindrical connector receptacle body 346 has an outer diameter which is substantially the same as that of the moving element 334. In a case where the electrical connector 327 is mounted on the electrical connector receptacle 344, the moving element 334 is urged at the forward end of the connector receptacle body 346 and is moved toward a deep portion. The electrical contact receptacles 348 are arranged circumferentially so as to be opposed against the inner peripheral surface of the connector receptacle body 346, and an inner periphery thereof is substantially the same as a radius of the outer peripheral surface of the connecting element 334.

Figure 26:
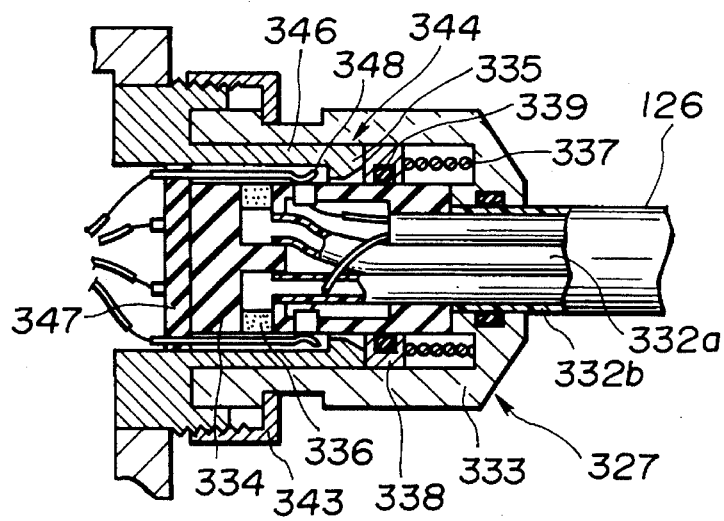

Accordingly, when operation is performed to mount the electrical connector 327 on the electrical connector receptacle 344, the electrical contact receptacles 348 move in sliding on the outer peripheral surface of the connecting element 334. An amount of projection is set such that, as shown in FIG. 26, the sides of the forward ends of the respective electrical contact receptacles 348 are in contact with the electrical contact 435 of the electrical connector 327.

Figure 27A:
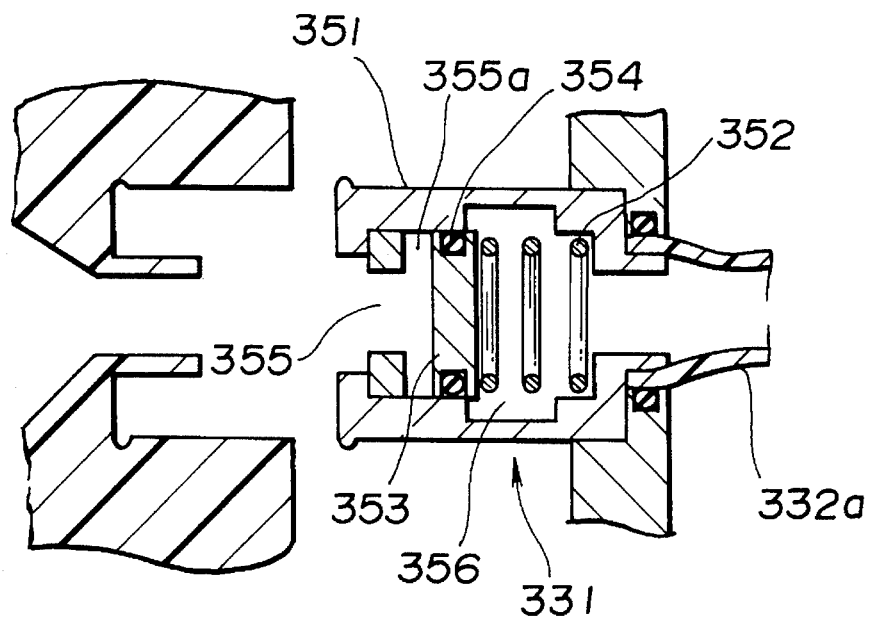
Figure 27B:
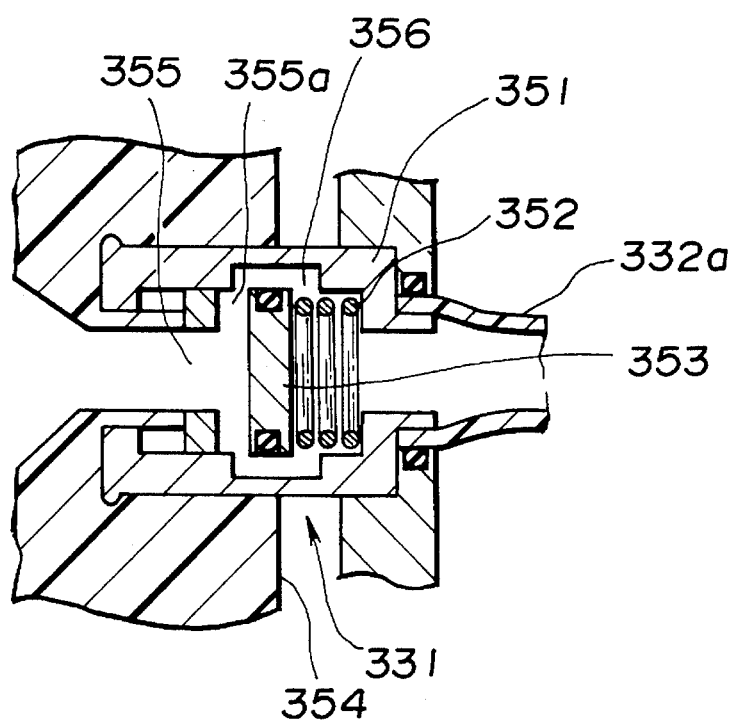

FIGS. 27a and 27b show a structure of the gas-feeding connector 331. A columnar movable element 353 biased forwardly (to the left) by a spring 352 is fitted into and is received within a cylindrical connector body 351. The connector body 351 has a proximal end thereof to which the gas-feeding tube 332a is connected. The gas-feeding tube 332a is sealed by a sealing element.

The movable element 353 has an outer peripheral surface on a lateral side thereof in which a groove is formed. An O-ring 354 is received in the groove. Under a condition illustrated in FIG. 27a, the gas-feeding connector 331 is closed in a liquid-tight structure. The movable element 353 has a forward end surface in which a recess 355 is formed. The recess 355 is provided with a passage 355a which opens at, for example, a pair of locations in an outer peripheral surface of a lateral side.

A pair of longitudinal grooves (in a lateral direction in FIG. 27a) 356 are formed in an inner peripheral surface in a connector body 351 at, for example, a pair of locations at positions deeper than a position in contact with the O-ring 354.

Meanwhile, an opening in the light source unit 325 has an inner diameter thereof which is fitted over the connector body 351. A ring-like projection 357 is provided on an inner side of the light source unit 325. When the gas-feeding connector 331 is mounted, the movable element 353 is urged and is moved by the projection 357 and is brought to a condition illustrated in FIG. 27b.

Under the condition, the passage 355a communicates with the longitudinal grooves 356. The heated air is fed toward the gas-feeding tube 332a.

The discharge connector 341 is also of a similar structure. In the present embodiment, the light guide connector 324 and the electrical connector 327 are under a liquid-tight condition as shown in FIG. 27a and FIG. 25 under a condition which is not connected to the light source unit 325 and the CCU 328.

The light guide connector 324 is connected to the light source unit 325, whereby the gas-feeding connector 331 and the discharge connector 341 open. The heated air is fed into the electrical connector 327 through the gas-feeding tube 332a to dry the sponge 336.

In a case where such operation is performed that the electrical connector 327 is mounted on the electrical connector receptacle 344, moisture is adhered to the outside of the electrical connector 327 in a case immediately after the surface of the movable element 338 has been dipped in disinfection liquid. Only wiping by cloth makes it impossible to perfectly remove the moisture which enters a gap between the outer peripheral surface of the connecting element 334 and the inner peripheral surface of the movable element 338.

Accordingly, in a case where the electrical connector 327 is pressed or forced into the electrical connector receptacle 344, the remaining moisture enters the electrical connector 327 when the moving element 338 is moved on the outer periphery of the connecting element 334. However, the remaining moisture is absorbed by the sponge 336 and does not reach the electrical contact 335. Thus, it is possible to prevent short-circuiting of the electrical contact 335 due to moisture.

The sponge 334 is brought to a dried condition after a while since, even if the sponge 334 absorbs the moisture, the heated air is always fed from the internal light source unit 325 through the gas-feeding tube 332a. After the endoscope inspection, in a case where the light guide connector 324 is disconnected from the light source unit 325, the gas-feeding connector 331 and the discharge connector 341 form a liquid-tight structure. Even if the electronic endoscope 322 is dipped in the disinfection liquid, the moisture does not entire the electrical connector 327, the gas-feeding connector 331 and the discharge connector 341. Accordingly, the sponge 336 within the electrical connector 327 maintains a dried condition.

For this reason, when used again after disinfection processing, even if moisture is adhered to the outside of the electrical connector 327, the moisture is absorbed and removed by the sponge 336 under a dried condition, whereby it is possible to reliably prevent a short-circuiting accident from occurring.

Figure 28:
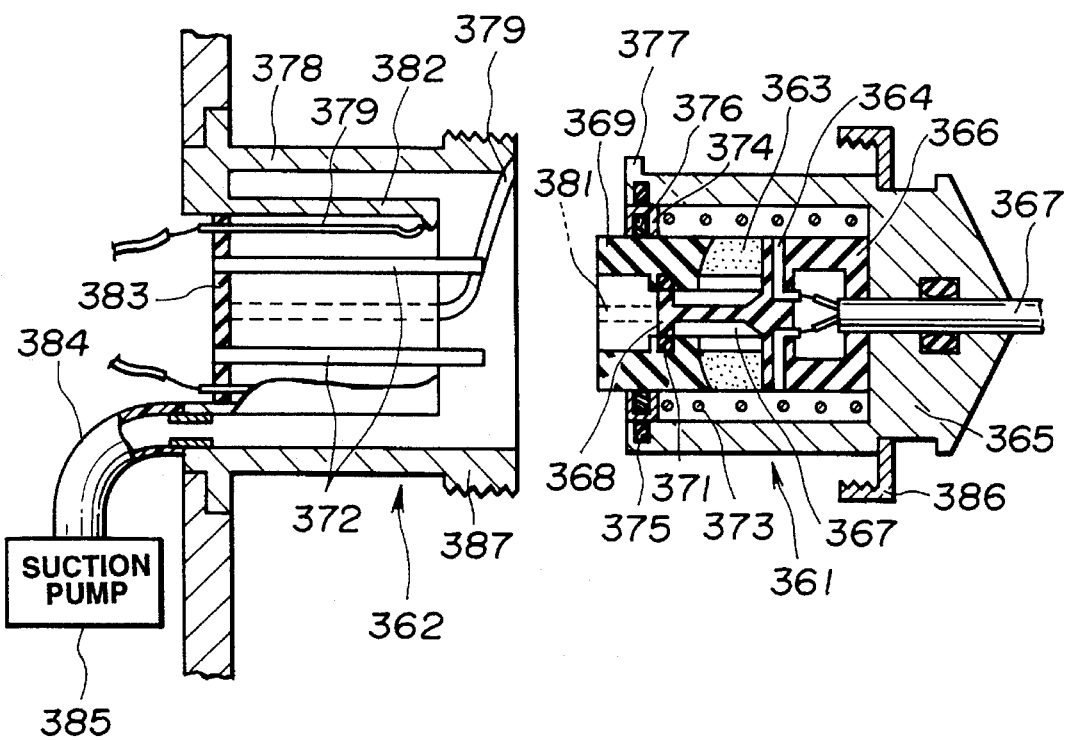
FIGS. 28 and 29 relate to an eighth embodiment of the invention, where.

FIG. 28 shows a structure in the vicinity of an electrical connector 361 and an electrical connector receptacle 362 in an eighth embodiment of the invention. In the sixth embodiment, the sponge 336 is dried by the fed air, whereas, in the seventh embodiment the sponge 363 is compressed by connection (mounting) between the electrical connector 361 and the electrical connector receptacle 362, to discharge the moisture contained in the sponge 363, and thereafter, the moisture at the electrical contact 364 of the electrical connector 361 is absorbed by the sponge 363.

The electrical connector 361 is such that an insulator 366 provided with a plurality of electrical contacts 364 is fixedly mounted within a connector body 365, and the electrical contacts 364 are connected to a signal line of a signal cable 367.

A diameter reduced portion 368 provided with a groove 367 in an outer peripheral surface thereof is formed on the insulator 366. A sponge 363 having resiliency and a moisture absorbing function and a first moving element 369 are arranged on the outside of the diameter reduced portion 368. (In the fifth embodiment, the first moving element 369 and the insulator 366 are integrated with each other. In the present embodiment, however, the first moving element 369 is movable).

A sealing element 371 is received in a peripheral groove in an inner peripheral surface of the first moving element 369. Thus, the eighth embodiment has a water-tight function between the first moving element 369 and the diameter reduced portion 368 which is fitted within the first moving element 369. The first moving element 369 is urged at mounting and is moved rearwardly (to the right in FIG. 28) by a projecting urging element 372 which is provided on an electrical connector receptacle 362. Upon the movement, the sponge 363 is compressed to discharge the moisture which is absorbed by the sponge 363.

A ring-like second moving element 374 which is biased forwardly by a spring 373 as in the sixth embodiment, is movably arranged between the outer peripheral surface of the first moving element 369 and the inner peripheral surface of the connector body 365. A pair of sealing elements 375 and 376 are provided on inner peripheral surfaces of the respective second moving element 374 and connector body 365, so as to have a liquid-tight function.

A projection 377 for positioning upon connection is provided on a front end of the connector body 365. A helical groove 379 is provided at a corresponding position in an inner peripheral surface of a cover portion 378 of the electrical connector receptacle 362. Accordingly, in a case where the electrical connector 361 is connected to the electrical connector receptacle 362, the side of the electrical connector 361 is connected so as to be rotated. In a case of the connecting operation, the pair of urging elements 372, for example, provided on the electrical connector receptacle 362 urge the front end surface of the first moving element 369 to move the same rearwardly.

The first moving element 369 is provided with a pair of recesses 381. In a case where the electrical connector 361 is rotated through 90° from the condition illustrated in FIG. 28, the urging elements 372 are received respectively within the recesses 381. The first moving element 369 is returned to its original condition prior to the movement caused by an elastic force of the sponge 363.

The plurality of electrical contact receptacles 379 which are protected by a ring-like projection 382 within the cover 378 are arranged on the electrical connector receptacle 362. The electrical contact receptacles 379 have respective proximal ends thereof which are fixedly mounted on a disc-like insulator 383. The electrical contact receptacles 379 are connected to a signal processing circuit (not shown). Moreover, the electrical connector receptacle 362 has a proximal end thereof which is connected to a suction pump 385 through a tube 384 which is provided with an opening. The moisture can be discharged from the sponge 363 and can be sucked and removed.

Furthermore, the electrical connector 361 is provided with a fixing ring 386 which is provided with a female screw, while the cover 378 of the electrical connector receptacle 362 is provided with a male screw 387.

Figure 29:
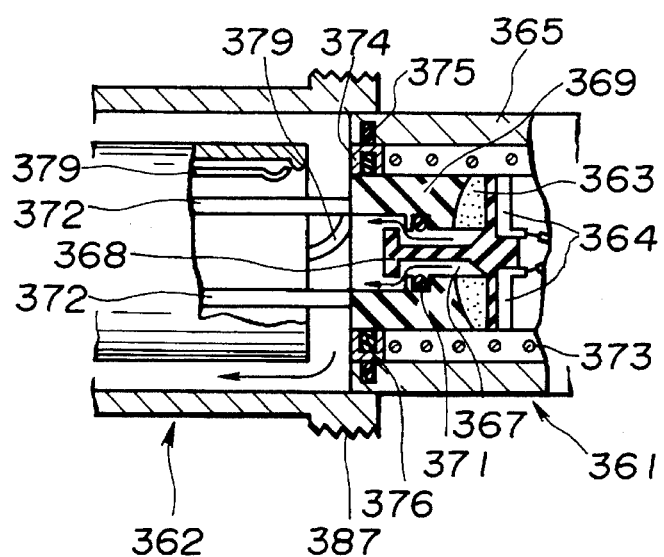

FIG. 29 shows the electrical connector 361 connected to the electrical connector receptacle 362. The electrical connector 361 is rotated through a rotational angle which is less than 90°, from FIG. 28. The sponge 363 is compressed by movement of the first moving element 369. Further, by the movement of the first moving element 369, a space on the inside of the sponge 363 communicates with the side of the electrical connector receptacle 362 through the peripheral groove 367. The moisture discharged from the sponge 363 is sucked toward the suction pump 385.

When the electrical connector 361 is further rotated from the condition illustrated in FIG. 29, the urging elements 372 are respectively received within the recesses 381, and the second moving element 369 is returned to its original condition prior to being moved. In a case where the electrical connector 361 is further moved toward the electrical connector receptacle 362 to perform connecting operation, the second moving element 374 is moved. Whereupon the moisture is absorbed by the sponge 363 and is removed, thereafter, the electrical contact receptacles 379 are respectively in contact with the electrical contacts 364.

According to the present embodiment, by mounting operation, the sponge 363 is compressed to discharge the absorbed moisture and, thereafter, the compression is returned to make it possible to absorb the moisture moving toward the electrical contacts 364 together with movement of the second moving element 374.

Figure 30:
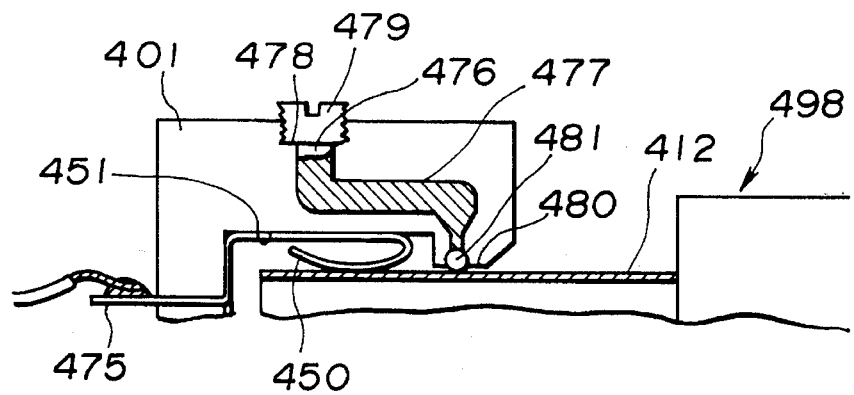
FIG. 30 is an arrangement view of a principal portion of means for applying a lubricant element having electric conductivity to an electrical contact portion of a connector having a liquid-tight arrangement.

As shown in FIG. 30, water repellant conductive grease 477 may be applied to an electrical connector 498 similar to, for example, the electrical connector 35 in FIG. 4a to shed the water to thereby prevent short-circuiting from occurring. The electrical connector 498 is such that contact patterns 412 are exposed to a surface up to a front portion of the rearward wall thickened potion. Meanwhile, electrical contacts 450 are so provided as to be bent within the electrical connector receptacle 451 so as to be respectively in contact with the contact patterns 412. An outward contact 475 at proximal ends of the electrical contacts 450 is connected to a TV camera.

In FIG. 30, a grease receiving portion 476 which is filled with conductive grease is provided within a CCU 401. The grease receiving portion 476 has a pair of openings 480 (one of which is not shown) in an inner surface of an entrance portion of the electrical connector receptacle 451. Moreover, a closure or lid 479 is detachably mounted on a grease filling port 478 in the grease receiving portion 476. A roller element 481 in contact with a surface of the electrical connector 498 at the time the electrical connector 498 is inserted into the electrical connector receptacle 451 is provided at the opening 480 in the grease receiving portion 476.

With the arrangement described above, when the electrical connector 498 is inserted or is removed with respect to the electrical connector 498 is inserted or is removed with respect to the electrical connector receptacle 451, the roller element 481 is rotated in keeping with movement of the electrical connector 498, and the conductive grease 477 within the grease receiving portion 476 is applied to a surface of the electrical connector 498 through the opening 480. Accordingly, if attachment and detachment operations of the electrical connector are repeated, the conductive grease 477 is always applied to the surface of the electrical connector 498. Thus, water repellency of the electrical connector 498 is not degraded or depleted.

In connection with the above, the conductive grease 477 has a generally high resistance value. Accordingly, even if the conductive grease 477 is applied to the entire or whole surface of the electrical connector 498, if the spacing between the contact patterns 412 is sufficiently spaced, there is no case where the contact patterns 412 are short-circuited. Moreover, the contact patterns 412 on the side of the electrical connector 498 and the electrical contacts 450 on the side of the electrical connector receptacle 451 are in proximity to each other upon connection, and the conductive grease 477 is removed by a biasing force given to the electrical contacts 450. Thus, there is no fear of contact failure.

Figure 31A:
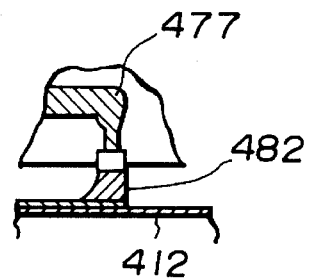
FIGS. 31a, 31b and 31c are enlarged views of a principal portion, respectively showing modifications of the applying means in FIG. 30.
Figure 31B:
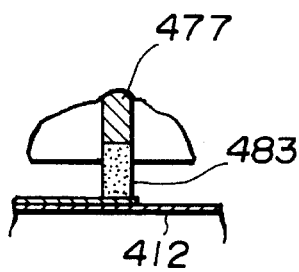
Figure 31C:
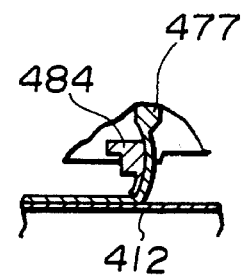

Furthermore, if the conductive grease 477 within the grease receiving portion 476 is reduced in amount, the closure 479 is demounted, and the grease should be supplemented from the filling port 478. In place of the roller element 481, a brush-like element 482 shown, for example, in FIG. 31a, a porous element 483 illustrated in FIG. 31b or a wiper-like element 484 as shown in FIG. 31c may be used.

Figure 32:
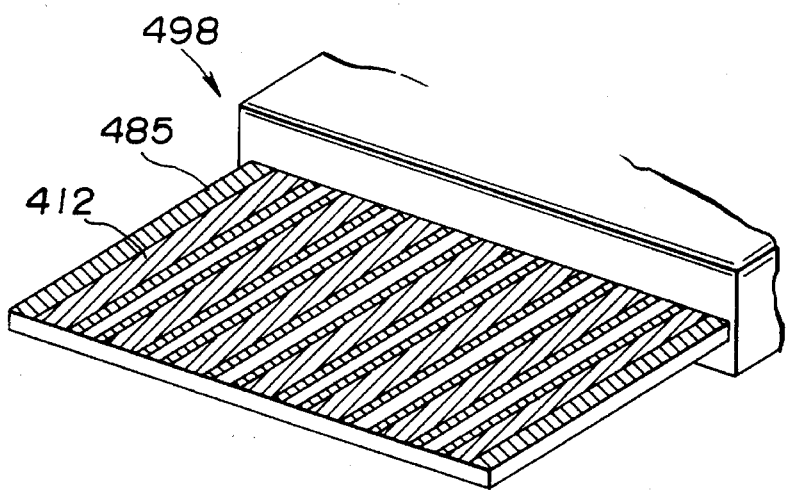
FIG. 32 is an explanatory view showing an applying scope or range of the lubricating element.

Further, as shown in FIG. 32, an applying region 485 of the grease toward the electrical connector 498 may be limited to a periphery or circumstance of the contact patterns 412. In this case, since a portion to which the conductive grease 477 is not applied is formed between the contact patterns 412, a distance between the contact patterns 412 is shortened. Thus, miniaturization of the electric connector 498 is made possible.

The above-described embodiments can be combined with each other to form different embodiments. These embodiments belong to the present invention.

Moreover, in the aforesaid embodiments, the endoscope has been described as an organism inserting device having an inserting section which is inserted into an organism. However, the invention should not be limited to the organism insertion device. For example, the invention can also be applied to an electrocautery device, for example, in which an electrode is inserted into an inserting section inserted into an organism, and high-frequency current from an exterior high-frequency power-source unit flows into a lesion part within the organism through the electrode, to cut off lesion tissues.

What is claimed is:

1. An endoscope apparatus comprising:

an endoscope including:

an inserting section capable of being inserted into an organism, illuminating-light means for projecting an illuminating light from an illuminating window which is provided at a forward end of said inserting section, observation means disposed within said inserting section for forming an image of a subject, said observation means including an electrical device for producing electrical image signals; and an electrical connector provided with a plurality of electrical contacts which are electrically connected to said electrical device, wherein said electrical device is electrically connected to said electrical connector through a signal cable; and liquid removing means provided within said electrical connector for removing liquid from said plurality of electrical contacts of said electrical connector.

2. An endoscope apparatus comprising:

an endoscope including:

an elongated inserting section capable of being inserted into an organism, illuminating-light means for projecting an illuminating light from an illuminating window provided at a forward end of said inserting section, observation means for forming an image of a subject, wherein said observation means includes an electrical device for producing electrical image signals and a first electrical connector provided with a plurality of electrical contacts which are electrically connected to said electrical device;

a control unit including:

a second electrical connector to which said first electrical connector is detachably connected, said second electrical connector having a plurality of electrical contacts which correspond to said plurality of electrical contacts of said first electrical connector; and liquid removing means provided within said control unit for removing liquid from said plurality of electrical contacts of said first electrical connector when first electrical connector is adjacent said second electrical connector.

3. An endoscope apparatus according to either claim 1 or 2, wherein said endoscope has a liquid-tight structure.

4. An endoscope apparatus according to claim 1, wherein said electrical connector has a liquid-tight structure.

5. An endoscope apparatus according to either claim 1 or 2, wherein said electrical device includes a photoelectric conversion image pickup element which generates said electrical image signals corresponding to said image of the subject.

6. An endoscope apparatus according to claim 1, wherein said liquid removing means includes gas-feeding means for blowing air against said plurality of electrical contacts of said electrical connector to remove said liquid.

7. An endoscope apparatus according to claim 2, wherein said liquid removing means blows heated air against said plurality of electrical contacts of said first electrical connector to remove said liquid.

8. An endoscope apparatus according to either claim 1 or 2, wherein said endoscope is an electronic endoscope including a photoelectric conversion image pickup element as said electrical device.

9. An endoscope apparatus according to either claim 1 or 2, wherein said endoscope includes an optical endoscope having an image guide for transmitting the subject image and a TV camera detachably mounted on said optical endoscope and having a photoelectric conversion image pickup element as said electrical device.

10. An endoscope apparatus according to either claim 1 or 2, wherein said inserting section is rigid.

11. An endoscope apparatus according to either claim 1 or 2, wherein said inserting section is flexible.

12. An endoscope apparatus according to claim 2, wherein said endoscope includes a light guide for transmitting the illuminating light supplied from a light-source unit to one of end surfaces of said light guide to project the illuminating light from said illuminating window.

13. An endoscope apparatus according to claim 12, wherein said liquid removing means includes gas-feeding means for blowing air containing heat generated by a light-source unit toward said plurality of electrical contacts of said first electrical connector.

14. An endoscope apparatus according to claim 2, wherein said liquid removing means includes time setting means for setting a predetermined period of time for removing the liquid in the vicinity of said plurality of electrical contacts of said first electrical connector.

15. An endoscope apparatus according to claim 2, wherein said liquid removing means includes a sensor for detecting liquid in the vicinity of said plurality of electrical contacts of said first electrical connector.

16. An endoscope apparatus according to claim 15, wherein said liquid removing means includes liquid control means for ON/OFF controlling of the liquid removing operation in accordance with a detecting result of said sensor.

17. An endoscope apparatus according to claim 2, wherein said first electrical connector includes an exposure portion on a side of a distal end of a surface of an insulator in which portions of said plurality of electrical contacts are exposed substantially flush with said surface of said insulator.

18. An endoscope apparatus according to claim 17, wherein said first electrical connector further includes a shield contact which is provided in the form of a ring surface on a side of an outer periphery of said exposure portion.

19. An endoscope apparatus according to claim 17, wherein said liquid removing means includes a humidity absorbing element which is provided in the entrance of a recess capable of receiving said insulator, for absorbing liquid.

20. An endoscope apparatus according to claim 19, wherein said liquid removing means includes a wiper means which is provided in the vicinity of the entrance of the recess capable of receiving said insulator for wiping liquid.

21. An endoscope according to claim 2, wherein said plurality of electrical contacts includes respective exposure portions which are exposed to a surface of an insulator, and wherein said exposure portions are liquid-tightly covered by a sliding element which is biased by a biasing element.

22. An endoscope apparatus according to claim 21, wherein said first electrical connector includes said sliding element in which, whenever said first electrical connector and said second electrical connector are detachably connected to each other, said second electrical connector urges said sliding element to expose said exposure portion.

23. An endoscope apparatus according to claim 22, wherein said liquid removing means includes a liquid absorbing element which is provided on a surface of said insulator distally of said exposure portion.

24. An endoscope apparatus according to claim 23, wherein said liquid removing means further includes drying means for supplying air to said liquid absorbing element.

25. An endoscope apparatus according to claim 24, wherein said liquid removing means includes a liquid releasing mechanism for compressing said liquid absorbing element to thereby release the absorbed liquid.

26. An endoscope apparatus according to claim 2, wherein said liquid removing means includes heating means provided in the vicinity of said plurality of electrical contacts of said second electrical connector, the liquid in the vicinity of said plurality of electrical contacts of said first electrical connector being heated by said heating means to thereby remove said liquid in the vicinity of said plurality of electrical contacts of said first electrical connector.

27. An endoscope apparatus according to claim 2, wherein said control unit includes control means for controlling starting and stopping of operation of said liquid removing means.

28. An endoscope apparatus according to claim 2, wherein said control unit includes automatic connecting means for mechanically connecting said first electrical connector and said second electrical connector after completion of operation of said liquid removing means.

29. An endoscope apparatus according to claim 2, wherein said control unit causes said liquid removing means to operate whenever said first electrical connector and said second electrical connector are mechanically connected to each other.

30. An endoscope apparatus according to claim 29, wherein, whenever said liquid removing means is operated, said control unit turns off electrical current flow through said second electrical connector.

31. An endoscope apparatus according to claim 29, wherein said control unit includes a sensor for detecting whether or not liquid remains at said first electrical connector, and wherein operation of said liquid removing means is controlled by a detecting output from said sensor.

32. An organism inserting unit comprising:

an organism inserting device including:

an elongated inserting section capable of being inserted into an organism;

an electrical device for producing electrical signals; and a first electrical connector provided with a plurality of electrical contacts which are electrically connected to said electrical device by a signal cable, said first electrical connector having a liquid-tight structure, a control unit including:

a second electrical connector to which said first electrical connector is detachably connected, said second electrical connector having a plurality of electrical contacts which correspond to said plurality of electrical contacts of said first electrical connector;

an electrical circuit electrically connected to said second electrical connector by a signal cable, for electrically energizing said electrical device, and liquid removing means disposed adjacent said second electrical connector for removing liquid from said plurality of electrical contacts of said second electrical connector.

33. An organism inserting unit according to claim 32, wherein said organism inserting device has a liquid-tight structure.

34. An endoscope apparatus according to either claim 32, wherein said electrical device includes a photoelectric conversion image pickup element for generating an electrical signal corresponding to said subject image, and wherein said electrical circuit includes an image-signal processing circuit which performs signal processing with respect to said image pickup element to generate an image signal for displaying said subject image.

* * * * *